US008143192B2

(12) United States Patent
Metzlaff et al.

(10) Patent No.: US 8,143,192 B2
(45) Date of Patent: Mar. 27, 2012

(54) METHODS FOR INCREASING THE RESISTANCE OF PLANTS TO HYPOXIC CONDITIONS

(75) Inventors: Michael Metzlaff, Tervuren (BE); Marc De Block, Merelbeke (BE)

(73) Assignee: Bayer Cropscience N.V., Ghent (BE)

( * ) Notice: Subject to any disclaimer, the term of this patent is extended or adjusted under 35 U.S.C. 154(b) by 980 days.

(21) Appl. No.: 11/917,729

(22) PCT Filed: Jun. 6, 2006

(86) PCT No.: PCT/EP2006/005393
§ 371 (c)(1),
(2), (4) Date: Dec. 14, 2007

(87) PCT Pub. No.: WO2006/133827
PCT Pub. Date: Dec. 21, 2006

(65) Prior Publication Data
US 2009/0064371 A1    Mar. 5, 2009

Related U.S. Application Data

(60) Provisional application No. 60/691,103, filed on Jun. 16, 2005.

(30) Foreign Application Priority Data

Jun. 15, 2005  (EP) .................................... 05076392

(51) Int. Cl.
*A01N 25/00* (2006.01)
(52) U.S. Cl. .................................................... 504/116.1
(58) Field of Classification Search .................. None
See application file for complete search history.

(56) References Cited

U.S. PATENT DOCUMENTS

| 4,742,060 | A | 5/1988 | Shiokawa et al. |
| 4,845,106 | A | 7/1989 | Shiokawa et al. |
| 4,849,432 | A | 7/1989 | Shiokawa et al. |
| 6,362,393 | B1 * | 3/2002 | Konzak et al. ............... 800/260 |
| 6,753,296 | B1 * | 6/2004 | Senn et al. ................... 504/221 |
| 2005/0044594 | A1 | 2/2005 | Schmulling et al. |

FOREIGN PATENT DOCUMENTS

| CA | 2 100 924 | 1/1994 |
| EP | 0 192 606 | 8/1986 |
| EP | 0 302 389 | 2/1989 |
| EP | 0 376 279 | 7/1990 |
| EP | 0 649 845 | 4/1995 |
| WO | WO 91/04965 | 4/1991 |
| WO | WO 99/37789 | 7/1999 |
| WO | WO 99/53050 | 10/1999 |
| WO | WO 00/01133 | 1/2000 |
| WO | WO 00/04173 | * 1/2000 |
| WO | WO 01/26468 | * 4/2001 |
| WO | WO 02/059294 | 8/2002 |
| WO | WO 02/081500 | 10/2002 |
| WO | WO 03/008540 | 1/2003 |
| WO | WO 03/096811 | * 11/2003 |
| WO | WO 2004/090140 | 10/2004 |
| WO | WO 2004/095926 | 11/2004 |
| WO | WO 2006/045633 | 5/2006 |

OTHER PUBLICATIONS

Amor, et al. (Nov. 11, 1998) "The involvement of poly(ADP-ribose) polymerase in the oxidative stress responses in plants." FEBS Letters 440(1-2): 1-7.
Chen, et al. (1994) "Poly(ADP-ribose) polymerase in plant nuclei." Eur. J. Biochem. 224: 135-142.
Hunt, et al. (2004) "NAD—new roles in signalling and gene regulation in plants." New Phytologist 163: 31-44.
Matsuda, et al. (Nov. 1, 2001) "Neonicotinoids: insecticides acting on insect nicotinic acetylcholine receptors." Trends in Pharmacological Sciences 22(11): 573-580.
O'Farrell (1995) "ADP-ribosylation reactions in plants." Biochimie 77: 486-491.
Panda, et al. (Jul. 2002) "*tej* Defines a Role for Poly(ADP-Ribosyl)ation in Establishing Period Length of the *Arabidopsis* Circadian Oscillator." Developmental Cell 3: 51-61.
Payne and Bal (1976) "Cytological detection of poly(ADP-ribose) polymerase." Exp Cell Res 99: 428-432.
Placke and Weber (1993) "Method of determining imidacloprid residues in plant materials." Pflanzenschutz-Nachrichten Bayer 46 2: 109-182.
Tomizawa, et al. (2005) "Neonicotinoid insecticide toxicology: Mechanisms of selective action." Annual Review of Pharmacology and Toxicology 45: 247-268.
Willmitzer and Wagner (1982) Chapter 13: Poly(ADP-ribose) Synthesis in Plants pp. 241-252.

\* cited by examiner

*Primary Examiner* — Cynthia Collins
(74) *Attorney, Agent, or Firm* — Hunton & Williams LLP

(57) ABSTRACT

Methods are provided for increasing the resistance of plants to hypoxic or anoxic conditions. Such methods may be applied to increase the penetrance of plant roots in the growth medium or into soil. The methods according to the invention may include providing plants with a stress tolerance gene. Similar effects can be obtained by applying chemical compounds, including neonicotinoid compounds, to the plants.

8 Claims, 7 Drawing Sheets

METHODS FOR INCREASING THE RESISTANCE OF PLANTS TO HYPOXIC CONDITIONS

CROSS-REFERENCE TO RELATED APPLICATIONS

This application is the U.S. National Stage filing of International Application No. PCT/EP2006/005393, filed Jun. 6, 2006, which claims priority to EP 05076392.9, filed Jun. 15, 2005 and U.S. Provisional Patent Application No. 60/691,103, Jun. 16, 2005, the disclosures of each of which are hereby incorporated by reference.

Methods are provided for increasing the resistance of plants to hypoxic or anoxic conditions. Such methods may be applied to increase the penetrance of plant roots in the growth medium or into soil. The methods according to the invention may include modification of the genome of the plants by providing such plants with an exogenous stress tolerance gene or with a stress tolerant variant of an endogenous gene corresponding to such an exogenous gene. The methods according to the invention may also include applying neonicotinoid compounds, such as but not limited to imidacloprid, nitenpyram, acetamiprid, thiacloprid, thiamethoxam, clothianidin, and dinotefuran, to plants or their habitats, or to cells or seeds thereof. Particularly effective neonicotinoid compounds are neonicotinoid compounds which comprise a chloropyridine side chain, such as imidacloprid, nitenpyram, acetamiprid, and thiacloprid, particularly those during the degradation of which in plants 6-chloronicotininc acid (6-CNA) can be set free, like, e.g., imidacloprid and thiacloprid. The plants or their habitats can also be treated directly with 6-CNA.

BACKGROUND ART

Plants engineered to be stress tolerant are known in the art. Stress tolerance in plant cells and plants can, e.g., be achieved by reducing the activity or the level of the endogenous poly-ADP-ribose polymerases (PARP) or poly(ADP-ribose) glycohydrolases (PARG) as described in WO00/04173 and WO04/090140, respectively.

European patent application No. 04077624.7 describes that stress tolerance in plants and plant cells is achieved using nucleotide sequences encoding enzymes involved in the NAD salvage synthesis pathway and/or the NAD de novo synthesis pathway e.g. for overexpression in plants.

However, none of these documents disclose the possibility to use the stress tolerance genes mentioned therein for obtaining tolerance to hypoxic or anoxic conditions in plant cells and plants. Neither do they disclose the use of the stress tolerance genes described therein for the purpose of allowing the root system of the plant to penetrate deeper into the growth medium or the soil.

The application of compounds of the class of neonicotinoids on plants for purposes other than insect control is also known from the art (WO 01/26468, WO 03/096811).

WO 01/26468 discloses a method of improving the growth of plants comprising applying to the plants or the locus thereof at least one compound selected from the class of the neonicotinoids.

WO03/096811 describes that the yield and/or the vigor of an agronomic plant can be increased or improved in locations where the level of insect infestation below that indicating the need for the use of an insecticide for insect control purposes by treating a seed of the plant with a neonicotinoid compound. The method is deemed useful for non-transgenic plants and for plants having a foreign gene that encodes for the production of a modified *Bacillus thuringiensis* delta-endotoxin protein.

None of these documents however describe the use of compounds of the class of the neonicotinoids on plants for the purpose of increasing the tolerance of plant cells or plants to hypoxic or anoxic conditions or to allow the root system of the plant to penetrate deeper into the growth medium or the soil.

Thus, the art remains silent on methods to increase the depth of penetration of a root system or roots of a plant into the growth medium or soil, or to increase tolerance of plant cells or plants to hypoxic or anoxic stress conditions using stress tolerance genes or by application of a chemical compound of the neonicotinoid class to plants, or cells thereof as described hereinafter in the different embodiments and claims.

SUMMARY OF THE INVENTION

In one embodiment of the invention, a novel method of increasing the tolerance of plant cells or plants to hypoxic or anoxic conditions is provided comprising, providing the plant cells or plants with a stress tolerance enhancing transgene, wherein the stress tolerance enhancing transgene is selected from:
  a stress tolerance enhancing transgene capable of reducing the expression of plant endogenous PARP genes, particularly wherein the transgene codes for a PARP inhibitory RNA molecule
  a stress tolerance enhancing transgene capable of reducing the expression of plant endogenous PARG genes, particularly wherein the transgene codes for a PARG inhibitory RNA molecule; or
  a stress tolerance enhancing transgene coding for a plant-functional enzyme of the nicotinamide adenine dinucleotide salvage synthesis pathway selected from nicotinamidase, nicotinate phosphoribosyltransferase, nicotinic acid mononucleotide adenyl transferase or nicotinamide adenine dinucleotide synthetase.

In another embodiment, the invention relates to the use of such stress tolerance enhancing transgenes to increase the penetrance of plant roots in growth medium, including soil.

In yet another embodiment of the invention, a method for increasing the tolerance of plant cells or plants to hypoxic or anoxic conditions is provided comprising applying to the plant cell, plant or seed from which such plant is grown, or to the habitat thereof, an effective amount of a neonicotinoid compound.

In still another embodiment, the invention relates to the use of such compounds to increase the penetrance of plant roots in growth medium, including soil.

The invention further relates to a method for increasing the tolerance of plant cells or plants to hypoxic or anoxic conditions comprising the step of providing cells of said plant with an effective amount of 6-chloronicotinic acid.

The invention also relates to the use of 6-CNA for increasing the penetrance of plant roots into the growth medium.

The following populations were analysed:
Col-0: data points for wild-type *Arabidopsis* line
427-16: data points for *A. thaliana* transgenic line comprising anti-PARP2 gene with a weak tolerance to high light stress conditions
427-20: data points for *A. thaliana* transgenic line comprising anti-PARP2 gene with a weak tolerance to high light stress conditions
427-20: data points for *A. thaliana* transgenic line comprising anti-PARP2 gene with a moderate tolerance to high light stress conditions The graph represents a typical boxplot (or box and whisker plot) on the left of each of the groups of values, summarizing the following statistical measures:
median
upper and lower quartiles
minimum and maximum data values.

In addition, on the right hand for each of the groups of values, the mean and the standard error of the mean for those values is indicated.

The boxplot is interpreted as follows:
the box itself contains the middle 50% of the data. The upper edge (hinge) of the box indicates the $75^{th}$ percentile of the data set, and the lower hinge indicates the $25^{th}$ percentile. The range of the middle two quartiles is known as the inter-quartile range.
The line in the box indicates the median value of the data.
The ends of the whiskers indicate the minimum and maximum data values, unless outliers are present in which case the whiskers extend to the nearest value points within a range of 1.5 times the interquartile range.

Figure 3:
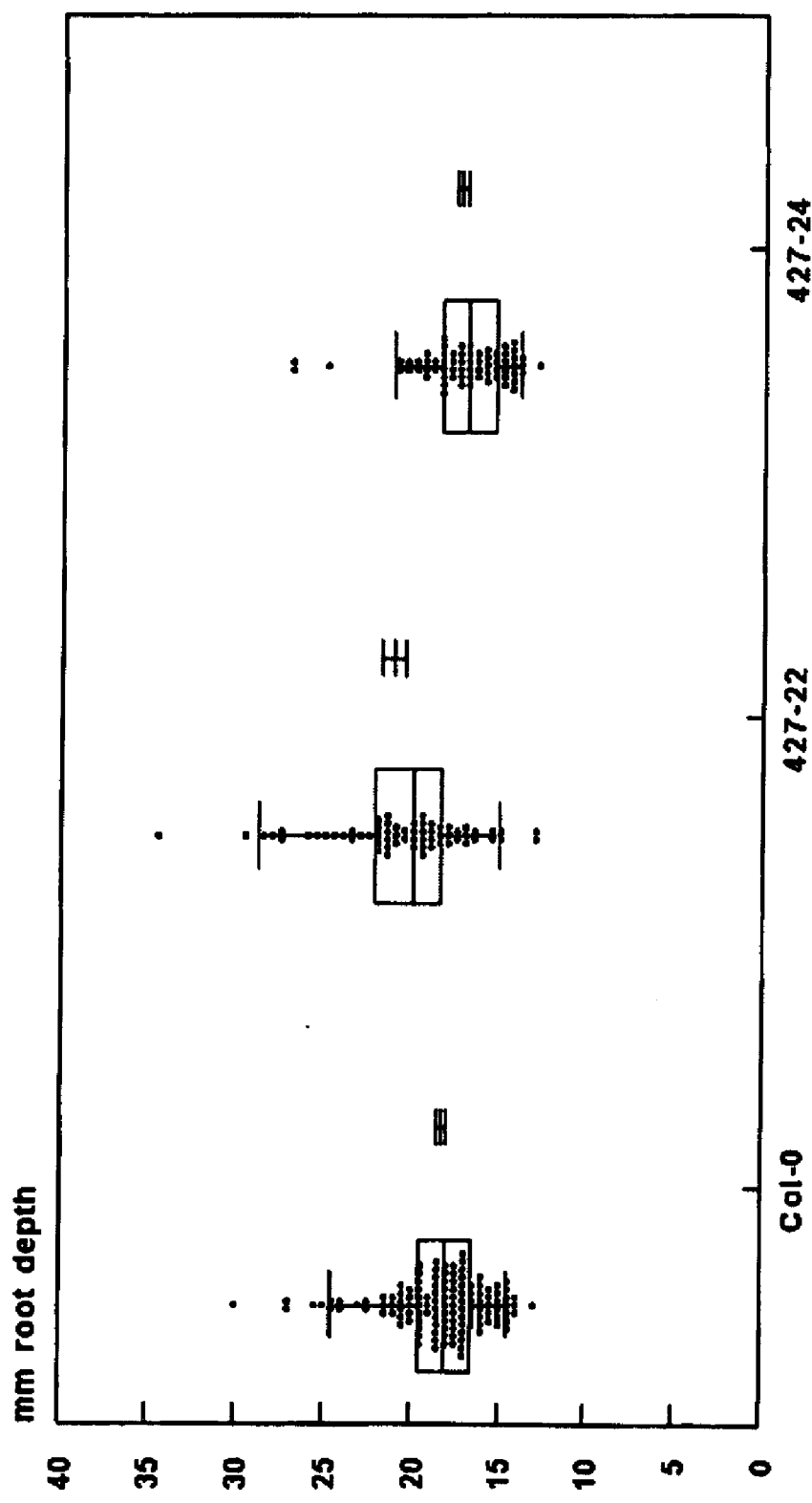

FIG. 3: Boxplot representation and standard error of the mean for the measured values for root depth (mm) of *Arabidopsis thaliana* cv. Col-plants comprising a transgene encoding a dsRNA molecule capable of reducing the expression of endogenous PARP genes.

Figure 4:
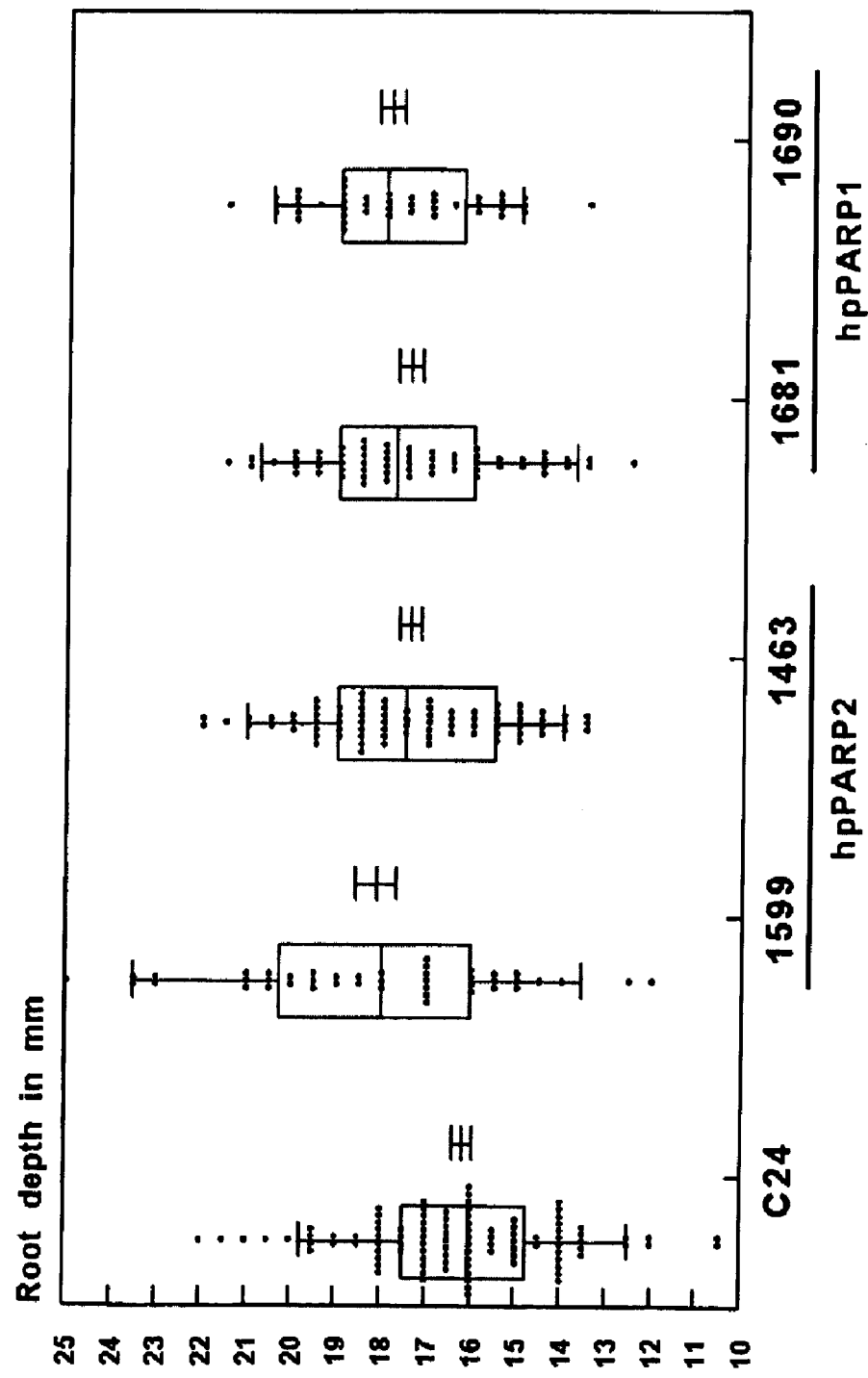

The following populations were analyzed:
Col-0: data points for wild-type *Arabidopsis* line
427-22: data points for *A. thaliana* transgenic line comprising anti-PARP2 gene with a high tolerance to high light stress conditions
427-24: data points for *A. thaliana* transgenic line comprising anti-PARP2 gene with a low tolerance to high light stress conditions FIG. 4: Boxplot representation and standard error of the mean for the measured values for root depth (mm) of *Arabidopsis thaliana* cv. C24-plants comprising a transgene encoding a dsRNA molecule capable of reducing the expression of endogenous PARP genes.

Figure 5:
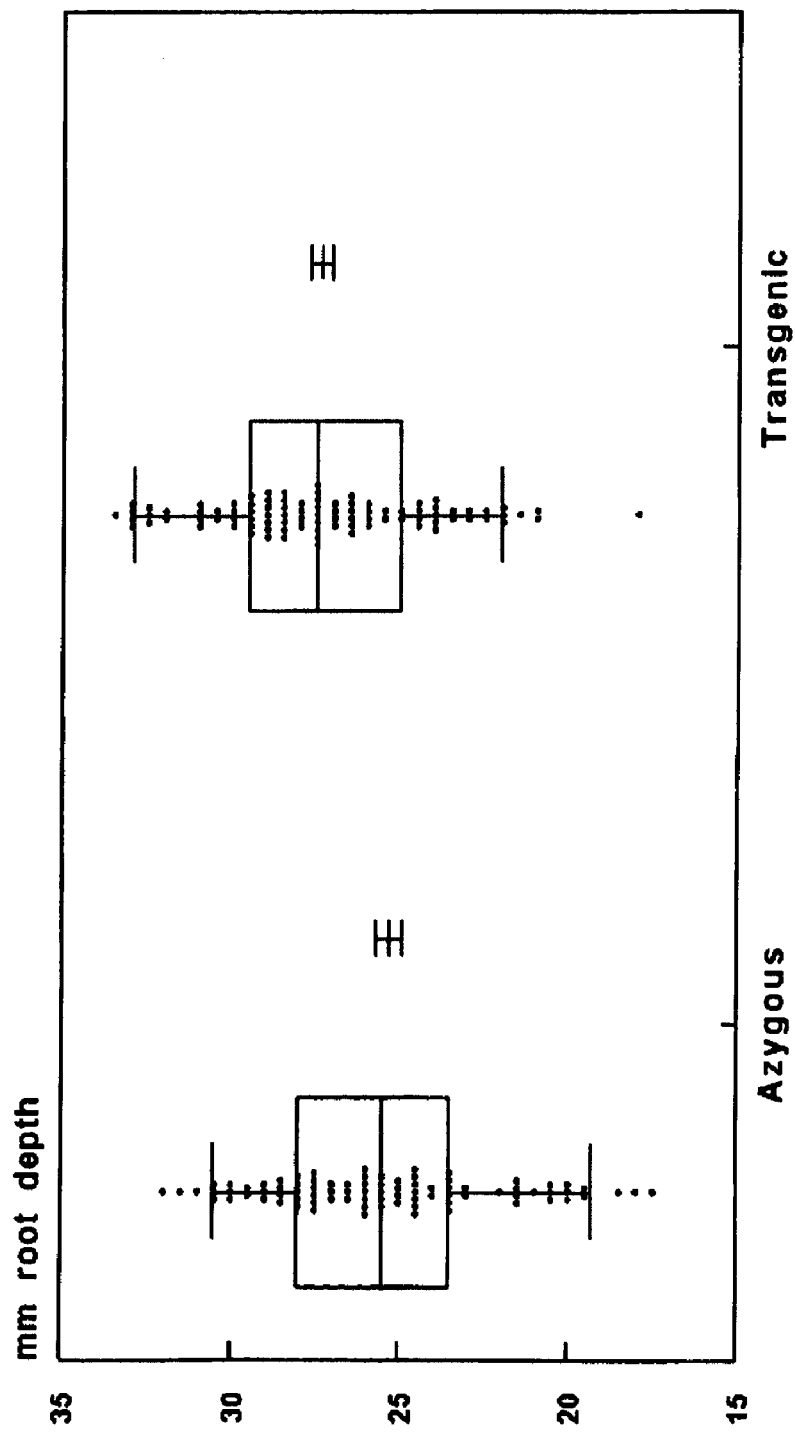

The following populations were analyzed:
C24: data points for wild-type *Arabidopsis* line
1599: data points for *A. thaliana* transgenic line comprising anti-PARP2 gene with a high tolerance to high light stress conditions
1463: data points for *A. thaliana* transgenic line comprising anti-PARP2 gene with a moderate tolerance to high light stress conditions
1681: data points for *A. thaliana* transgenic line comprising anti-PARP1 gene with a moderate tolerance to high light stress conditions
1690: data points for *A. thaliana* transgenic line comprising anti-PARP1 gene with a moderate tolerance to high light stress conditions FIG. 5: Boxplot representation and standard error of the mean for the measured values for root depth (mm) measured on an *A. thaliana* Col-0 population segregating for the anti-PARP2 transgene.

The following populations were analyzed:
Azygous: data points for *A. thaliana* plants from the population which do not contain an anti-PARP2 gene
Transgenic: data points for *A. thaliana* plants from the population which contain an anti-PARP2 gene FIG. 6: Boxplot representation and standard error of the mean for the measured values for root depth (mm) of *Arabidopsis thaliana* cv. C24 plants treated with various concentrations of imidacloprid as compared to untreated *Arabidopsis thaliana* cv. C24 plants.

Figure 7:
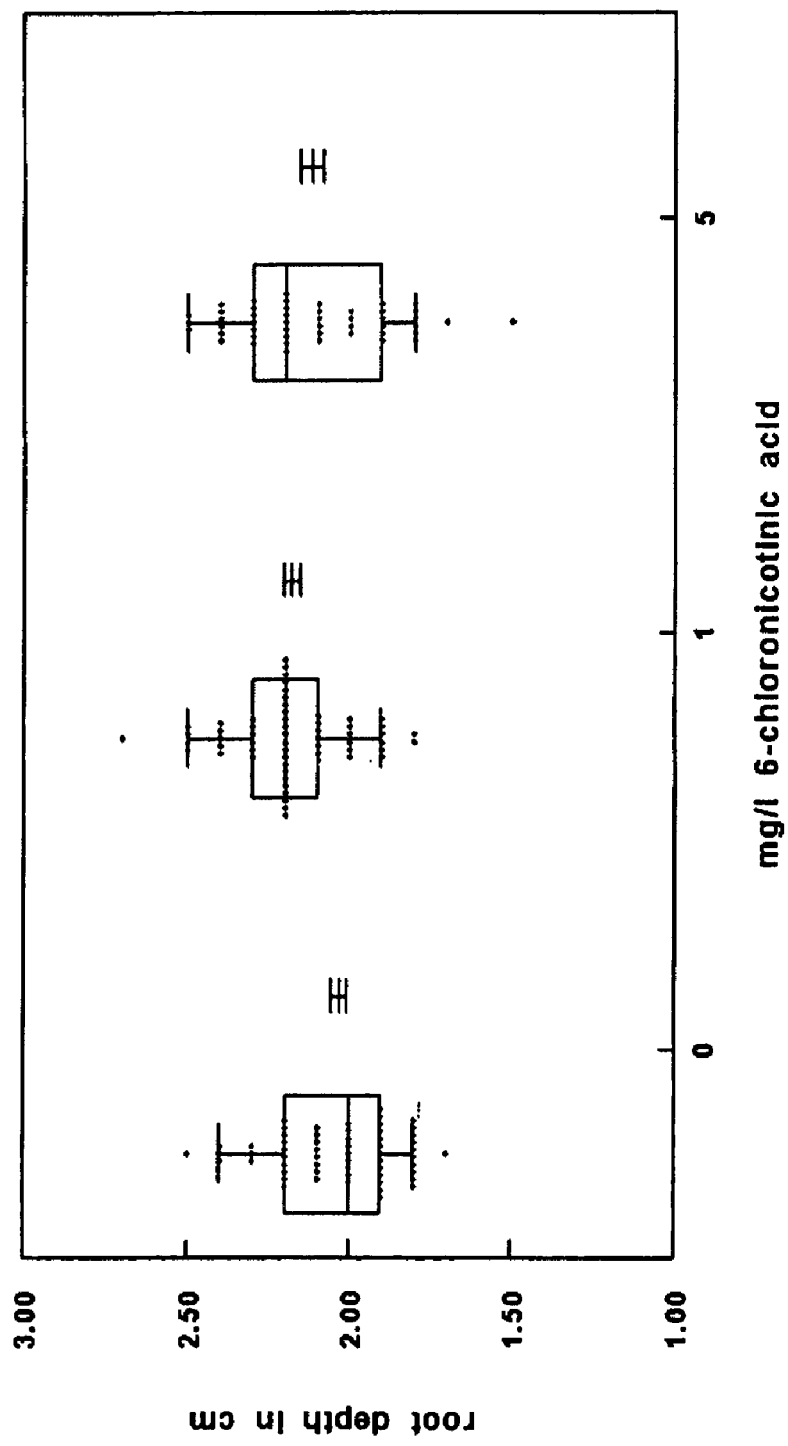

The following populations were analyzed:
0: untreated *A. thaliana* C24 plants
50: *A. thaliana* C24 plants treated with 50 mg/L imidacloprid
100: *A. thaliana* C24 plants treated with 100 mg/L imidacloprid FIG. 7: Boxplot representation and standard error of the mean for the measured values for root depth (mm) of *Arabidopsis thaliana* cv. C24 plants treated with various concentrations of 6-chloronicotinic acid as compared to untreated *Arabidopsis thaliana* cv. C24 plants.

The following populations were analyzed:
0: untreated *A. thaliana* C24 plants
1: *A. thaliana* C24 plants treated with 1 mg/L 6-chloronicotinic acid
5: *A. thaliana* C24 plants treated with 5 mg/L 6-chloronicotinic acid

DETAILED DESCRIPTION

The current invention is based on the realization that plants comprising stress tolerance genes, such as the chimeric genes encoding dsRNA targeted for silencing the expression of parp1 or parp2 genes of plants, developed a root system with roots that protruded deeper into the growth medium than the roots of control plants. The deeper penetration of the roots has remained unnoticed with the plants comprising stress tolerance genes as described in the prior art and required the development of a particular assay, as described herein, to analyze statistically the root penetrance into the medium.

Although not intending to limit the invention to a particular mode of action, it is thought that the stress tolerance genes increase the tolerance of plant cells, including the plant cells of roots to hypoxic or anoxic conditions, thereby allowing the roots comprising such a stress tolerance gene to grow in less favourable oxygen conditions, as can be found in the deeper areas of a growth medium or the deeper soil layers, where the oxygen tension is lower. The increased penetrance of the root system of plants into the deeper layers of the soil, provides a partial explanation for the increased drought resistance under field conditions observed for plants comprising the stress tolerance genes as described herein, such as the dsRNA encoding genes silencing the expression of the endogeneous parp1 or parp2 genes.

A similar effect on the root protrusion could be observed in described assay after addition of compound of the neonicotinoid class or 6-chloronicotinic acid. The effect of the application of neonicotinoids on root growth depth is independent of the presence of insects which are the targets of the above-mentioned neonicotinoids. Accordingly, the effect is also connected with the biochemical improvement of stress tolerance, particularly hypoxia- or anoxia-related stress tolerance, of a plant or plant cell or the seed from which it is grown.

Accordingly, in a first embodiment, the invention is directed towards the use of a stress tolerance enhancing transgene to increase the tolerance of a plant cell, plant or seed to hypoxic or anoxic conditions.

As used herein, "hypoxic or anoxic conditions" refer to conditions to which plant cells, plants or parts of such plants are exposed wherein the availability of oxygen is low to very low. Anoxic conditions refer to conditions where there is almost no oxygen available. Typically, conditions wherein the dissolved oxygen concentration is below about 2 mg/L, are indicated as hypoxic (0.1 mg/L to 2 mg/L), conditions wherein the dissolved oxygen is below 0.1 mg/L, particularly below 0.05 mg/L are indicated as anoxic. Normal dissolved oxygen concentration in water is about 8 mg/L. Hypoxic conditions in soil refer to those conditions where the oxygen tension is low, particularly where oxygen drops below 5% in the soil atmosphere.

Hypoxic conditions may occur e.g. upon flooding of the plants or parts of the plants. Hypoxic conditions may also occur where oxygen consumption is high, such as in soil layers comprising a lot of organic debris in the process of metabolization by microorganisms. Furthermore, hypoxic conditions occur in the deeper layers of a growth medium where diffusion of oxygen occurs from the surface. Hypoxic conditions also occur in the deeper layers of the soil as oxygen diffusion and consequently oxygen tension decreases from the surfaces. The rate of decrease in oxygen depends on the compactness of the soil (whereby the more compact the soil, the less soil atmosphere is present), the presence of decomposing organic material, water content etc.

As used herein, "a stress tolerance enhancing transgene" refers to a transgene which when introduced or expressed in a plant cell or plant, provides the cell or the plant with a better tolerance to stress which is brought on a plant, e.g., by the application of chemical compounds (e.g., herbicides, fungicides, insecticides, plant growth regulators, adjuvants, fertilizers), exposure to abiotic stress (e.g., drought, waterlogging, submergence, high light conditions, high UV radiation, increased hydrogen peroxide levels, extreme (high or low) temperatures, ozone and other atmospheric pollutants, soil salinity or heavy metals, hypoxia, anoxia, etc.) or biotic stress (e.g., pathogen or pest infection including infection by fungi, viruses, bacteria, insects, nematodes, mycoplasmas and mycoplasma like organisms, etc.).

Such a stress tolerance enhancing transgene may be a transgene capable of reducing the expression and/or the activity of poly(ADP-ribose)polymerase (PARP) gene in the plant cells or plants as described in WO 00/04173 or EP 04077984.5 (herein incorporated by reference).

Poly(ADP-ribose) polymerase (PARP), also known as poly(ADP-ribose) transferase (ADPRT) (EC 2.4.2.30), is a nuclear enzyme found in most eukaryotes, including vertebrates, arthropods, mollusks, slime moulds, dinoflagellates, fungi and other low eukaryotes with the exception of yeast. The enzymatic activity has also been demonstrated in a number of plants (Payne et al., 1976; Willmitzer and Wagner, 1982; Chen et al., 1994; O'Farrell, 1995).

PARP catalyzes the transfer of an ADP-ribose moiety derived from $NAD^+$, mainly to the carboxyl group of a glutamic acid residue in the target protein, and subsequent ADP-ribose polymerization. The major target protein is PARP itself, but also histones, high mobility group chromosomal proteins, topoisomerase, endonucleases and DNA polymerases have been shown to be subject to this modification.

As a particular embodiment, the stress tolerance enhancing transgene may comprise the following operably linked DNA fragments:

a) a plant-expressible promoter;
b) a DNA region which when transcribed results in an RNA molecule capable of reducing the expression of the endogenous PARP encoding genes of a plant (a PARP inhibitory RNA molecule);
c) a DNA region involved in transcription termination and polyadenylation.

The mentioned DNA region may result upon transcription in a so-called antisense RNA molecule reducing in a transcriptional or post-transcriptional manner the expression of a PARP encoding gene in the target plant or plant cell, comprising at least 20 or 21 consecutive nucleotides having at least 95% to 100% sequence identity to the complement of the nucleotide sequence of a PARP encoding gene present in the plant cell or plant.

The mentioned DNA region may also result in a so-called sense RNA molecule comprising reducing in a transcriptional or post-transcriptional manner the expression of a PARP encoding gene in the target plant or plant cell, comprising at least 20 or 21 consecutive nucleotides having at least 95% to 100% sequence identity to the nucleotide sequence of a PARP encoding gene present in the plant cell or plant.

However, the minimum nucleotide sequence of the antisense or sense RNA region of about 20 nt of the PARP coding region may be comprised within a larger RNA molecule, varying in size from 20 nt to a length equal to the size of the target gene. The mentioned antisense or sense nucleotide regions may thus be about from about 21 nt to about 5000 nt long, such as 21 nt, 40 nt, 50 nt, 100 nt, 200 nt, 300 nt, 500 nt, 1000 nt, 2000 nt or even about 5000 nt or larger in length. Moreover, it is not required for the purpose of the invention that the nucleotide sequence of the used inhibitory PARP RNA molecule or the encoding region of the transgene, is completely identical or complementary to the endogenous PARP gene the expression of which is targeted to be reduced in the plant cell. The longer the sequence, the less stringent the requirement for the overall sequence identity is. Thus, the sense or antisense regions may have an overall sequence identity of about 40% or 50% or 60% or 70% or 80% or 90% or 100% to the nucleotide sequence of the endogenous PARP gene or the complement thereof. However, as mentioned antisense or sense regions should comprise a nucleotide sequence of 20 consecutive nucleotides having about 100% sequence identity to the nucleotide sequence of the endogenous PARP gene. Preferably the stretch of about 100% sequence identity should be about 50, 75 or 100 nt.

For the purpose of this invention, the "sequence identity" of two related nucleotide sequences, expressed as a percentage, refers to the number of positions in the two optimally aligned sequences which have identical residues (×100) divided by the number of positions compared. A gap, i.e. a position in an alignment where a residue is present in one sequence but not in the other is regarded as a position with non-identical residues. The alignment of the two sequences is performed by the Needleman and Wunsch algorithm (Needleman and Wunsch 1970) Computer-assisted sequence alignment, can be conveniently performed using standard software program such as GAP which is part of the Wisconsin Package Version 10.1 (Genetics Computer Group, Madison, Wis., USA) using the default scoring matrix with a gap creation penalty of 50 and a gap extension penalty of 3.

It will be clear that whenever nucleotide sequences of RNA molecules are defined by reference to nucleotide sequence of corresponding DNA molecules, the thymine (T) in the nucleotide sequence should be replaced by uracil (U). Whether reference is made to RNA or DNA molecules will be clear from the context of the application.

The efficiency of the above mentioned transgenes in reducing the expression of the endogenous PARP gene may be further enhanced by inclusion of DNA elements which result in the expression of aberrant, unpolyadenylated PARP inhibitory RNA molecules. One such DNA element suitable for that purpose is a DNA region encoding a self-splicing ribozyme, as described in WO 00/01133 A1.

The efficiency of the above mentioned transgenes in reducing the expression of the endogenous PARP gene of a plant cell may also be further enhanced by including into one plant cell simultaneously a transgene as herein described encoding a antisense PARP inhibitory RNA molecule and a transgene as herein described encoding a sense PARP inhibitory RNA molecule, wherein said antisense and sense PARP inhibitory RNA molecules are capable of forming a double stranded RNA region by base pairing between the mentioned at least 20 consecutive nucleotides, as described in WO 99/53050 A1.

As further described in WO 99/53050 A1, the sense and antisense PARP inhibitory RNA regions, capable of forming a double stranded RNA region may be present in one RNA molecule, preferably separated by a spacer region. The spacer region may comprise an intron sequence. Such a transgene may be conveniently constructed by operably linking a DNA fragment comprising at least 20 nucleotides from the isolated or identified endogenous PARP gene, the expression of which is targeted to be reduced, in an inverted repeat, to a plant expressible promoter and 3' end formation region involved in transcription termination and polyadenylation. To achieve the construction of such a transgene, use can be made of the vectors described in WO 02/059294 A1.

Current nomenclature refers to the classical Zn-finger-containing polymerases as PARP1 proteins (and corresponding parp1 genes) whereas the structurally non-classical PARP proteins are currently referred to as PARP2 (and corresponding parp2 genes) and "PARP encoding genes" as used herein, may refer to either type.

The following database entries (herein incorporated by reference) identifying experimentally demonstrated and putative poly ADP-ribose polymerase protein sequences, parts thereof or homologous sequences, could be used according to the current invention: BAD53855 (*Oryza sativa*); BAD52929 (*Oryza sativa*); XP_477671 (*Oryza sativa*); BAC84104 (*Oryza sativa*); AAT25850 (*Zea mays*); AAT25849 (*Zea mays*); NP_197639 (*Arabidopsis thaliana*); NP_850165 (*Arabidopsis thaliana*); NP_188107 (*Arabidopsis thaliana*); NP_850586 (*Arabidopsis thaliana*); BAB09119 (*Arabidopsis thaliana*); AAD20677 (*Arabidopsis thaliana*); Q11207 (*Arabidopsis thaliana*); C84719 (*Arabidopsis thaliana*); T51353 (*Arabidopsis thaliana*); T01311 (*Arabidopsis thaliana*); AAN12901 (*Arabidopsis thaliana*); AAM13882 (*Arabidopsis thaliana*); CAB80732 (*Arabidopsis thaliana*); CAA10482 (*Arabidopsis thaliana*); AAC79704 (*Zea mays*); AAC19283 (*Arabidopsis thaliana*); CAA10888 (*Zea mays*); CAA10889 (*Zea mays*); CAA88288 (*Arabidopsis thaliana*).

As a particular embodiment of the invention, the PARP gene expression reducing gene may comprise the following operably linked DNA fragments:

a) a plant expressible promoter
b) a DNA region which when transcribed yields an RNA molecule, the RNA molecule comprising:
   a. An antisense nucleotide sequence comprising at least about 20 consecutive nucleotides having about 96% sequence identity to a nucleotide sequence of about 20 consecutive nucleotides selected from the nucleotide sequences of SEQ ID 1 (Arabidopsis parp1 coding region) SEQ ID 2 (Arabidopsis parp2 coding region) SEQ ID 3 (*Zea mays* parp1 coding region), SEQ ID 4 (another *Zea mays* parp1 coding region), SEQ ID 5 (*Zea mays* parp2 coding region) or SEQ ID 6 (cotton parp2 partial cDNA) or from nucleotide sequences encoding proteins with similar or identical amino acid sequences as encoded by the mentioned nucleotide sequences.
   b. A sense nucleotide sequence comprising at least about 20 nucleotides which are complementary to the antisense nucleotide sequence. The sense nucleotide sequence may thus comprise a sequence of at least about 20 consecutive nucleotides having about 96% sequence identity to a nucleotide sequence of about 20 consecutive nucleotides selected from the nucleotide sequences of SEQ ID 1 (Arabidopsis parp1 coding region) SEQ ID 2 (Arabidopsis parp2 coding region) SEQ ID 3 (*Zea mays* parp1 coding region), SEQ ID 4 (another *Zea mays* parp1 coding region), SEQ ID 5 (*Zea mays* parp2 coding region) or SEQ ID 6 (cotton parp2 partial cDNA) of from nucleotide sequences encoding proteins with similar or identical amino acid sequences as encoded by the mentioned nucleotide sequences;
      whereby the sense and antisense nucleotide sequence are capable of forming a double stranded RNA molecule (dsRNA);
c) A DNA region for transcription termination and polyadenylation.

However, it will be clear that other PARP gene expression reducing genes as described in WO00/04173 or EP 04077984.5 may be used.

In another embodiment of the invention, the stress tolerance enhancing transgene may be a transgene capable of reducing the expression and/or the activity of the PARG encoding genes of the plants or plants cells, as described e.g. in WO 2004/090140 (herein incorporated by reference).

PARG (poly(ADP-ribose) glycohydrolase; E.C.3.2.1.143) converts poly(ADP-ribose) polymers to free ADP-ribose by its exoglycosidase and endoglycosidase activity (PARG).

In plants, a poly(ADP-ribose) glycohydrolase has been identified by map-based cloning of the wild-type gene inactivated in a mutant affected in clock-controlled transcription of genes in *Arabidopsis* and in photoperiod dependent transition from vegetative growth to flowering (tej). The nucleotide sequence of the gene can be obtained from nucleotide databases under the accession number AF394690 (Panda et al., 2002 Dev. Cell. 3, 51-61; SEQ ID No 7)

Nucleotide sequences of other plant PARG encoding genes from plants can be found in WO 2004/090140 A2, such as the PARG gene from *Solanum tuberosum* (SEQ ID No 8); *Oryza sativa* (SEQ ID No 9) or *Zea mays* (SEQ ID No 10) as well as methods to isolate additional PARG encoding genes and variants thereof from other plants.

Thus, in one embodiment, the plants or plant cells engineered to be stress resistant may comprise the following operably linked DNA fragments:

a) a plant expressible promoter
b) a DNA region, which when transcribed yields an inhibitory RNA molecule, the RNA molecule comprising
  i. a antisense nucleotide region comprising at least 20 consecutive nucleotides having at least 96% sequence identity to a nucleotide sequence of about 20 nucleotides selected from the complement of a nucleotide sequence encoding a plant PARG protein, such as the nucleotide sequences of SEQ ID 7, SEQ ID 8, SEQ ID 9 or SEQ ID 10 or nucleotide sequences encoding proteins with similar or identical amino acid sequences as the nucleotide sequences mentioned; or
  ii. a sense nucleotide region comprising at least 20 consecutive nucleotides selected from a nucleotide sequence encoding a plant PARG protein, such as the nucleotide sequences of SEQ ID 7, SEQ ID 8, SEQ ID 9 or SEQ ID 10 or nucleotide sequences encoding proteins with similar or identical amino acid sequences as the nucleotide sequences mentioned; or
  iii. antisense and sense nucleotide sequences as mentioned sub i) or ii) whereby said antisense and sense nucleotide sequence are capable of forming a double stranded RNA molecule;
c) A DNA region involved in transcription termination and polyadenylation.

It will be immediately clear to the skilled artisan that additional parameters of length of sense and antisense nucleotide sequences or dsRNA molecules, and sequence identity for the ParG inhibitory RNA molecules can be used as mentioned above for the PARP inhibitory RNA molecules.

In yet another embodiment of the invention, the stress tolerance enhancing transgene may a transgene coding for a plant-function enzyme of the nicotineamide adenine dinucleotide salvage synthesis pathway. Accordingly, the stress tolerance enhancing gene may comprise the following operably linked DNA molecules:

a) a plant-expressible promoter;
b) a DNA region coding for a plant-functional enzyme of the nicotinamide adenine dinucleotide salvage synthesis pathway selected from nicotinamidase, nicotinate phosphoribosyltransferase, nicotinic acid mononucleotide adenyl transferase or nicotinamide adenine dinucleotide synthetase; and
c) a 3' end region involved in transcription termination and polyadenylation,
as described in EP 04077624.7 (herein incorporated by reference).

As used herein, "a plant-functional enzyme of the nicotinamide adenine dinucleotide salvage synthesis pathway" is an enzyme which when introduced into plants, linked to appropriate control elements such as plant expressible promoter and terminator region, can be transcribed and translated to yield a enzyme of the NAD salvage synthesis pathway functional in plant cells. Included are the enzymes (and encoding genes) from the NAD salvage synthesis, which are obtained from a plant source, but also the enzymes obtained from yeast (*Saccharomyces cereviseae*) or from other yeasts or fungi. It is thought that the latter proteins may be even more suitable for the methods according to the invention, since these are less likely to be subject to the enzymatic feedback regulation etc. to which similar plant-derived enzymes may be subject.

Enzymes involved in the NAD salvage synthesis pathway comprise the following

Nicotinamidase (EC 3.5.1.19) catalyzing the hydrolysis of the amide group of nicotinamide, thereby releasing nicotinate and NH3. The enzyme is also known as nicotinamide deaminase, nicotinamide amidase, YNDase or nicotinamide amidohydrolase Nicotinate phosphoribosyltransferase (EC 2.4.2.11) also known as niacin ribonucleotidase, nicotinic acid mononucleotide glycohydrolase; nicotinic acid mononucleotide pyrophosphorylase; nicotinic acid phosphoribosyltransferase catalyzing the following reaction

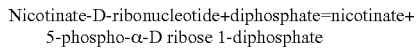

Nicotinate-D-ribonucleotide+diphosphate=nicotinate+ 5-phospho-α-D ribose 1-diphosphate Nicotinate-nucleotide adenylyltransferase, (EC 2.7.7.18) also known as deamido-NAD+ pyrophosphorylase; nicotinate mononucleotide adenylyltransferase; deamindonicotinamide adenine dinucleotide pyrophsophorylase; NaMT-ATase; nicotinic acid mononucleotide adenylyltransferase catalyzing the following reaction

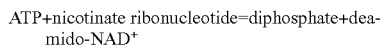

ATP+nicotinate ribonucleotide=diphosphate+deamido-NAD+

NAD-synthase (EC 6.3.1.5) also known as NAD synthetase; NAD+ synthase; nicotinamide adenine dinucleotide synthetase; diphosphopyridine nucleotide synthetase, catalyzing the following reaction

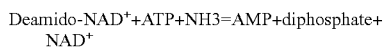

Deamido-NAD++ATP+NH3=AMP+diphosphate+ NAD+

In one embodiment of the invention, the DNA regions coding for a plant functional enzyme of the NAD salvage pathway may comprise a nucleotide sequence from SEQ ID Nos 11, 12, 13, 14 or 15 or a nucleotide sequence encoding a protein with similar or identical amino acid sequences as the proteins encoded by the above mentioned nucleotide sequences.

As described by Hunt et al., 2004, plant homologues of these enzymes have been identified and these DNA sequences may be used to similar effect (Hunt et al., 2004, New Phytologist 163(1): 31-44). The identified DNA sequences have the following Accession numbers: for nicotinamidase: At5g23220 (SEQ ID No 16); At5g23230 (SEQ ID No 17) and At3 g16190 (SEQ ID No 18); for nicotinate phosphoribosyltransferase: At4g36940 (SEQ ID No 19), At2g23420 (SEQ ID No 20), for nicotinic acid mononucleotide adenyltransferase: At5g55810 (SEQ ID No 21) and for NAD synthetase: At1g55090 (SEQ ID No 22).

However, it will be clear that the plants engineered to be stress resistant may also comprise variants of these nucleotide sequences, including insertions, deletions and substitutions thereof. Equally, homologues to the mentioned nucleotide sequences from species different from *Saccharomyces cerevisea* can be used. These include but are not limited to nucleotide sequences from plants, and nucleotide sequences encoding proteins with the same amino acid sequences, as well as variants of such nucleotide sequences.

Variants of the described nucleotide sequence will have a sequence identity which is preferably at least about 80%, or 85 or 90% or 95% with identified nucleotide sequences encoding enzymes from the NAD salvage pathway, such as the ones identified in the sequence listing. Preferably, these variants will encode functional proteins with the same enzymatic activity as the enzymes from the NAD salvage pathway.

Having read the above description of the use according to the invention of stress tolerance enhancing transgenes to increase tolerance of plant cells, plants or seeds to hypoxic or anoxic conditions, the skilled person will immediately realize that similar effects can be obtained using variants of an endogenous gene corresponding to such a stress tolerance enhancing transgene, which variant results in higher stress tolerance of the plant cells or plants harbouring such a variant. By way of example, variants of an endogenous parp2 gene of a plant, having a low expression level and providing the harbouring plant with increased stress tolerance could be used in a similar way as a transgene reducing the expression of the endogenous parp2 gene. Such variants gene can be introduced into plant cells or plants by breeding techniques.

A person skilled in the art will also be aware that expression of the different stress tolerance enhancing genes or transgenes may lead to a population of different events, which exhibit a distribution of effects ranging from almost no effect to a very pronounced effect. However, a person skilled in the art will clearly be able to distinguish, identify or isolate those representatives of a population that best suit the needs.

In another embodiment, the invention provides a method for increasing the penetrance of the roots of a plant into growth medium or soil comprising the step of providing the plant with a stress tolerance enhancing transgene, or with a endogenous variant of such stress tolerance enhancing transgene, as herein described in its different embodiments.

Figure 1:
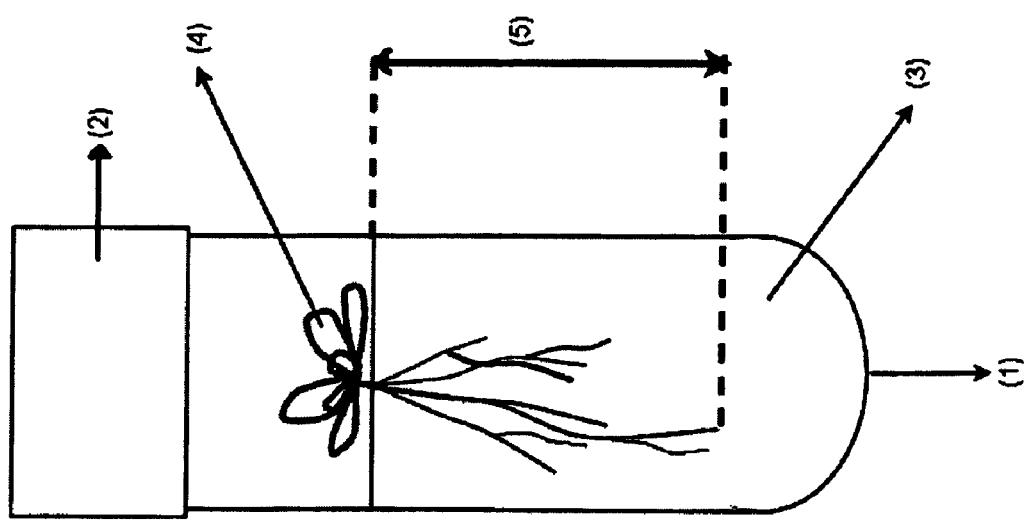
FIG. 1: Schematic representation of the assay to measure root depth of a plant growing in a agar solution. A container (1) with a seal (2) is filled with a transparent or translucent growth medium (3), such as 0.4% agar-water or 0.7% agar-water, to which additional test-compounds may be added. One pregerminated seed is added to the tube and allowed to grow for three weeks. After three weeks of growth in vertical position, the root depth (5) of the plant (4) is measured from the top of the medium to the lowest point of the roots.

As used herein, "protrusion of plant roots" or "the penetrance of the roots of a plant into growth medium or soil" refers to the depth of the growth of roots in solid growth medium, including soil, as measured from the surface of the growth medium to the lowest point of the roots (see also FIG. 1).

As a rule, an "increase in the protrusion or penetrance of plant roots" means at least a statistically significant increase in the depth of the growth of roots in growth medium as measured from the surface of the medium to the lowest point of root growth, which can be measured either as a difference in a comparison of the root depth of wild-type reference plants versus the root depth of plants engineered to be stress tolerant, or as a difference in a comparison of the root depth of plants treated with particular chemical compounds versus the root depth of untreated plants.

For a correct understanding of the invention, it is important to realize that deeper penetration of a root system of a plant into the growth medium or soil, achieved by the methods according to the invention, is not to be equalled with an increase of the root system in volume or dry or fresh weight. Indeed, the volume of a root system may be increased significantly, while the roots all remain quite superficial below the surface of the growth medium or soil. By contrast, roots of plants treated according to the invention may be equal in size, volume, weight or even length, yet protrude much deeper below the surface of the growth medium or the soil.

As used herein, "growth medium" is intended to refer to any medium suitable for plant growth including soil. Such media may include solidified or gellified liquids, such as water-agar, peat, turf, different types of soil etc.

In another embodiment, the invention is directed towards the use of a compound of the neonicotinoid class to increase the tolerance of a plant cell, plant or seed to hypoxic or anoxic conditions. Thus, a method is provided to increase the tolerance of a plant cell, plant or seed to hypoxic or anoxic conditions comprising the step of applying an effective amount of a neonicotinoid compound of the formula (I) to the plant cells, plants or seeds or to the habitat of the plants, or to the growth medium.

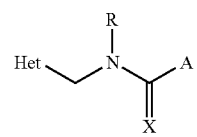

(I)

wherein

Het represents a heterocycle which is in each case optionally mono- or polysubstituted by fluorine, chlorine, methyl or ethyl, which heterocycle is selected from the following group of heterocycles:

pyrid-3-yl, pyrid-5-yl, 3-pyridinio, 1-oxido-5-pyridinio, 1-oxido-5-pyridinio, tetrahydrofuran-3-yl, thiazol-5-yl, A represents $C_1$-$C_6$-alkyl, —N($R^1$)($R^2$) or S($R^2$), in which $R^1$ represents hydrogen, $C_1$-$C_6$-alkyl, phenyl-$C_1$-$C_4$-alkyl, $C_3$-$C_6$-cycloalkyl, $C_2$-$C_6$-alkenyl or $C_2$-$C_6$-alkynyl, and $R^2$ represents $C_1$-$C_6$-alkyl, $C_2$-$C_6$-alkenyl, $C_2$-$C_6$-alkynyl, —C(=O)—$CH_3$ or benzyl, R represents hydrogen, $C_1$-$C_6$-alkyl, $C_2$-$C_6$-alkenyl, $C_2$-$C_6$-alkynyl, —C(=O)—$CH_3$ or benzyl or together with $R^2$ represents the groups below:

—$CH_2$—$CH_2$—, —$CH_2$—$CH_2$—$CH_2$—, —$CH_2$—O—$CH_2$—, —$CH_2$—S—$CH_2$—, —$CH_2$—NH—$CH_2$—, —$CH_2$—N($CH_3$)—$CH_2$—, and X represents N—$NO_2$, N—CN or CH—$NO_2$.

Saturated or unsaturated hydrocarbon radicals, such as alkyl or alkenyl, can in each case be straight-chain or branched as far as this is possible, including in combination with heteroatoms, such as, for example, in alkoxy.

These compounds are known to have insecticidal activity (see, for example, EP-A1-192 606, EP-A2-580 533, EP-A2-376 279, EP-A2-235 725).

Compounds of the formula (I) which may be mentioned are the neonicotinoids listed in "The Pesticide Manual", 13$^{th}$ Edition, 2003 (British Crop Protection Council).

One compound is imidacloprid of the formula

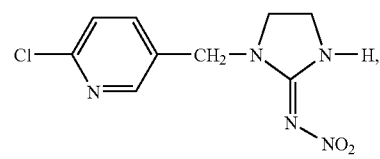

known, for example, from EP A10 192 060.

Another compound is nitenpyram of the formula

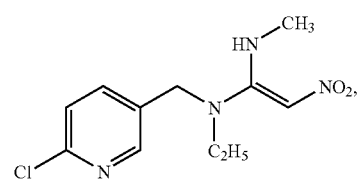

known, for example, from EP A2 0 302 389.

Another compound is acetamiprid of the formula

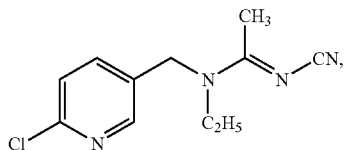

known, for example, from WO A1 91/04965.

Another compound is thiacloprid of the formula

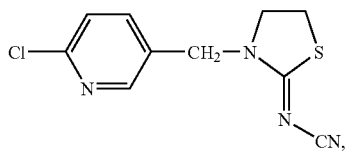

known, for example, from EP A2 0 235 725.

Another compound is thiamethoxam of the formula

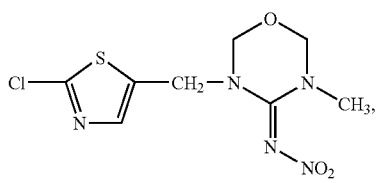

known, for example, from EP A2 0 580 553.

Another compound is clothianidin of the formula

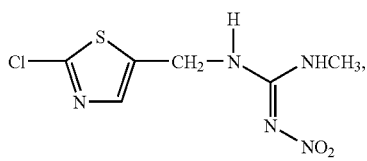

know, for example, from EP A2 0 376 279.

Another compound is dinotefuran of the formula

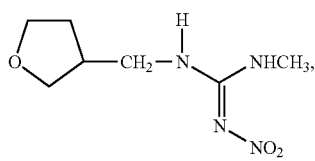

known, for example, from EP A1 0 649 845.

Particularly suited for the current inventions are compounds of the formula (I) wherein the substituent "Het" represents chloropyridyl

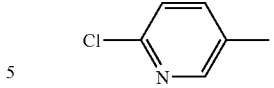

such as imidacloprid, nitenpyram, acetamiprid, and thiacloprid.

Particularly preferred compounds are imidacloprid and thiacloprid.

6-Chloronicotinic acid can be set free during the degradation of the above mentioned neonicotinoids which carry this group, such as imidacloprid, nitenpyram, and thiacloprid. For example, imidacloprid is degraded stepwise to the primary metabolite 6-chloronicotinic acid, which eventually breaks down into carbon dioxide. It was found that this metabolite also increases the stress tolerance and health of a plant or plant cell or seed from which such plant is grown and which is engineered to be stress tolerant and can be also be used according to the methods of the current invention.

One way of determining whether 6-CNA is set free during the degradation of the above mentioned neonicotinoids in plants or in particular plants is described by Placke and Weber (Pflanzenschutz-Nachrichten Bayer 46/1993, 2 109-182).

Thus, in another embodiment of the invention, a method is described which is useful to increase the tolerance of plants cells or plants or parts thereof to hypoxic or anoxic conditions comprising the step of providing to said plant, to a plant cell or to seed from which said plants are grown an effective amount of 6-chloronicotinic acid (niacin, CAS NO: 5326-23-8) of the formula (3)

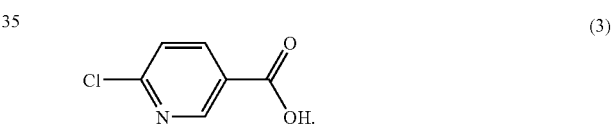

The effective amount of 6-chloronicotinic acid may be provided to the plant cell, plant or seed by applying directly the compound of the formula (3) to the plant cell, plant, seed and/or the habitat thereof. However, the 6-CNA may also be provided to the plant by providing a compound which can be metabolized by the plant to yield 6-CNA as a metabolite, such as the compounds mentioned above.

It will be immediately clear that the above described compounds can also be used to increase the penetrance of the roots of a plant into growth medium or soil comprising the step of providing an effective amount of a neonicotinoid compound of the formula (I), such as a neonicotinoid compound of the formula (I) comprising a chloropyridine side chain, particularly those neonicotinoids of the formula I comprising a chloropyridine side chain which can be metabolized in plants to yield 6-CNA, including imidacloprid or thiacloprid or providing 6-CNA to the plant cells, plants or seeds or to the habitat of the plants or to the growth medium.

One of the advantages of the present invention is that the systemic properties of the compounds according to the invention and compositions comprising said compounds mean that treatment of the seed of plants with these compositions is sufficient to increase the protrusion of the roots of the germinating plant and the resulting plant after emergence.

In another embodiment of the invention, a method is described which is useful to increase the protrusion of the roots of a plant, comprising applying to said plant and/or its habitat, to a plant cell or to seed from which said plants are grown an effective amount of a composition comprising the compounds of the formula (I).

Accordingly, the invention also relates to compositions comprising the compounds of the formula (I) for the use of such compositions according to the invention.

The compounds of formula (I) can be used also in a mixture with other active compounds, for example, insecticides, bactericides, miticides, fungicides, etc. in the form of their commercially useful formulations or in the application forms prepared from such formulations. This can be done to obtain compositions which in addition to increasing the protrusion of plant roots according to the invention also to combat pests which may be present. Insecticides which can be used are, for example, organophosphorous agents, carbamate agents, carboxylate type chemicals, chlorinated hydrocarbon type chemicals, insecticidal substances produced by microbes, etc.

In many cases, this results in synergistic effects, i.e. the activity of the mixture exceeds the activity of the individual components. Such formulations and application forms are commercially and ecologically especially useful as generally lower amounts of active ingredients can be used. A synergist, however, must not necessarily be active itself, as long as it enhances the action of the active compound.

A mixture with other known active compounds, such as herbicides, or with safeners, fertilizers and growth regulators is also possible.

Treatment according to the invention of the plants and plant parts with the active compounds is carried out directly or by allowing the compounds to act on their surroundings, environment or storage space by the customary treatment methods, for example by immersion, spraying, evaporation, fogging, scattering, painting on and, in the case of propagation material, in particular in the case of seed, also by applying one or more coats.

The active compounds can be converted into the customary formulations, such as solutions, emulsions, wettable powders, suspensions, powders, dusts, pastes, soluble powders, granules, suspension-emulsion concentrates, natural and synthetic materials impregnated with active compound, and microencapsulations in polymeric substances.

The content of the active compounds of the present invention in a commercially useful formulation or application form can be varied in a wide range. The active-compound content of the use forms prepared from the commercial formulations can vary within wide limits.

These formulations are produced in a known manner, for example by mixing the active compounds with extenders, that is liquid solvents and/or solid carriers, optionally with the use of surfactants, that is emulsifiers and/or dispersants, and/or foam-formers.

If the extender used is water, it is also possible to employ for example organic solvents as auxiliary solvents. Essentially, suitable liquid solvents are: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and also their ethers and esters, ketones such as acetone, methyl ethyl ketone, methyl isobutyl ketone or cyclohexanone, strongly polar solvents such as dimethylformamide and dimethyl sulphoxide, and also water.

As solid carriers there are suitable: for example ammonium salts and ground natural minerals such as kaolins, clays, talc, chalk, quartz, attapulgite, montmorillonite or diatomaceous earth, and ground synthetic minerals, such as highly disperse silica, alumina and silicates; as solid carriers for granules there are suitable: for example crushed and fractionated natural rocks such as calcite, marble, pumice, sepiolite and dolomite, and also synthetic granules of inorganic and organic meals, and granules of organic material such as sawdust, coconut shells, maize cobs and tobacco stalks; as emulsifiers and/or foam-formers there are suitable: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolysates; as dispersants there are suitable: for example lignin-sulphite waste liquors and methylcellulose.

Tackifiers such as carboxymethylcellulose and natural and synthetic polymers in the form of powders, granules or lattices, such as gum arabic, polyvinyl alcohol and polyvinyl acetate, as well as natural phospholipids such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyes, such as alizarin dyes, azo dyes and metal phthalocyanine dyes, and trace nutrients such as salts of iron, manganese, boron, copper, cobalt, molybdenum and zinc.

The formulations generally comprise between 0.1 and 98% by weight of active compound, preferably between 0.1 and 90% and particularly preferably between 0.5 and 70% by weight of active compound.

The effect of the neonicotinoid compounds and 6-CNA on root growth depth is particularly strongly pronounced at certain application rates. However, the application rates of the active compounds can be varied within relatively wide ranges. In general, the rates of applications are from 1 g to 1600 g of the active compound per hectare, preferably from 10 g to 800 g of the active compound per hectare, and particularly preferably from 10 g to 600 g of the active compound per hectare As mentioned before, the invention relates to methods which are useful to increase the protrusion of the roots of a plant into the growth medium or to increase the tolerance to hypoxia conditions, comprising applying to the plant propagation material including seed from which the plant is grown an effective amount of a composition comprising the compounds of the formula (I). The plant propagation material may be treated before planting, for example seed may be dressed before sowing. The compounds according to the invention may also be applied to seed grains either by impregnating the grains with a liquid formulation or by coating them with a solid formulation. The composition may also be applied to the planting site when the propagation material is being planted, e.g. during sowing.

In connection with the treatment of plant propagation material such as seeds, favourable rates of application are in general 0.1 to 1000 g, in particular 1 to 800 g, preferably 10 to 500 g of one of the neonicotinoid compounds or 6-CNA per 100 kg of material to be treated.

All plants and plant parts can be treated in accordance with the invention. Plant parts are to be understood to mean all above-ground and underground parts and organs of plants, such as shoot, leaf, flower and root, examples which may be mentioned being leaves, needles, stalks, stems, flowers, fruit bodies, fruits, seeds, roots, tubers and rhizomes. The plant parts also include harvested material, and vegetative and generative propagation material, for example cuttings, tubers, rhizomes, offsets and seeds. They also include plant cells, such as may be used or result from the transformation of a plant cell in accordance with the invention. It is also possible to apply the aforementioned compounds onto or into the soil, e.g. before planting or sowing to achieve the effect described, e.g. to enhance the stress tolerance of the plants after planting and the emerging plant which grows from a seed which has been sown into treated soil.

It will also be immediately clear that the methods of the invention comprising the use of stress tolerance enhancing transgenes or stress tolerance enhancing endogenous variants can be combined with the methods of the invention comprising the use of a neonicotinoid compound or 6-CNA, to yield additive and synergistic effects in increasing the tolerance to hypoxic or anoxic conditions or in increasing the root depth of a plant in a growth medium or soil.

The method of the current invention may be suitable for any plant, both dicotyledonous and monocotyledonous plants including but not limited to cotton, Brassica vegetables, oilseed rape, wheat, corn or maize, barley, sunflowers, rice, oats, sugarcane, soybean, vegetables (including chicory, lettuce, tomato), tobacco, potato, sugarbeet, papaya, pineapple, mango, Arabidopsis thaliana, but also plants used in horticulture, floriculture or forestry, cereal plants including wheat, oat, barley, rye, rice, turfgrass, sorghum, millet or sugarcane plants. The methods of the invention can also be applied to any plant including but not limited to cotton, tobacco, canola, oilseed rape, soybean, vegetables, potatoes, Lemna spp., Nicotiana spp., sweet potatoes, Arabidopsis, alfalfa, barley, bean, corn, cotton, flax, pea, rape, rice, rye, safflower, sorghum, soybean, sunflower, tobacco, wheat, asparagus, beet, broccoli, cabbage, carrot, cauliflower, celery, cucumber, eggplant, lettuce, onion, oilseed rape, pepper, potato, pumpkin, radish, spinach, squash, tomato, zucchini, almond, apple, apricot, banana, blackberry, blueberry, cacao, cherry, coconut, cranberry, date, grape, grapefruit, guava, kiwi, lemon, lime, mango, melon, nectarine, orange, papaya, passion fruit, peach, peanut, pear, pineapple, pistachio, plum, raspberry, strawberry, tangerine, walnut and watermelon.

As used herein "comprising" is to be interpreted as specifying the presence of the stated features, integers, steps or components as referred to, but does not preclude the presence or addition of one or more features, integers, steps or components, or groups thereof. Thus, e.g., a nucleic acid or protein comprising a sequence of nucleotides or amino acids, may comprise more nucleotides or amino acids than the actually cited ones, i.e., be embedded in a larger nucleic acid or protein. A transgene comprising a DNA region which is functionally or structurally defined, may comprise additional DNA regions etc.

Unless stated otherwise in the Examples, all recombinant DNA techniques are carried out according to standard protocols as described in Sambrook et al. (1989) Molecular Cloning: A Laboratory Manual, Second Edition, Cold Spring Harbor Laboratory Press, NY and in Volumes 1 and 2 of Ausubel et al. (1994) Current Protocols in Molecular Biology, Current Protocols, USA. Standard materials and methods for plant molecular work are described in Plant Molecular Biology Labfax (1993) by R. D. D. Croy, jointly published by BIOS Scientific Publications Ltd (UK) and Blackwell Scientific Publications, UK. Other references for standard molecular biology techniques include Sambrook and Russell (2001) Molecular Cloning: A Laboratory Manual, Third Edition, Cold Spring Harbor Laboratory Press, NY, Volumes I and II of Brown (1998) Molecular Biology LabFax, Second Edition, Academic Press (UK). Standard materials and methods for polymerase chain reactions can be found in Dieffenbach and Dveksler (1995) PCR Primer: A Laboratory Manual, Cold Spring Harbor Laboratory Press, and in McPherson at al. (2000) PCR—Basics: From Background to Bench, First Edition, Springer Verlag, Germany.

Throughout the description and Examples, reference is made to the following sequences:

SEQ ID No. 1: parp1 coding region from Arabidopsis thaliana.
SEQ ID No. 2: parp2 coding region from Arabidopsis thaliana.
SEQ ID No. 3: parp1 coding region 1 from Zea mays.
SEQ ID No. 4: parp1 coding region 2 from Zea mays.
SEQ ID No. 5: parp2 coding region from Zea mays.
SEQ ID No. 6: parp2 partial coding region from cotton.
SEQ ID No. 7: parG coding region from Arabidopsis thaliana.
SEQ ID No. 8: parG coding region from Solanum tuberosum.
SEQ ID No. 9: parG coding region from Oryza sativa.
SEQ ID No. 10: parG coding region from Zea mays.
SEQ ID No. 11: nucleotide sequence of the nicotinamidase from Saccharomyces cereviseae (PNC1).
SEQ ID No. 12: nucleotide sequence of the nicotinate phosphoribosyltransferase from Saccharomyces cereviseae (NPT1) (complement)
SEQ ID No. 13: nucleotide sequence of the nicotinic acid mononucleotide adenyl transferase 1 (NMA1) from Saccharomyces cereviseae.
SEQ ID No. 14: nucleotide sequence of the nicotinic acid mononucleotide adenyl transferase 2 (NMA2) from Saccharomyces cereviseae.
SEQ ID No. 15: nucleotide sequence of the NAD synthetase (QNS1) from Saccharomyces cereviseae.
SEQ ID No. 16: nucleotide sequence of the nicotinamidase from Arabidopsis thaliana (isoform 1).
SEQ ID No. 17: nucleotide sequence of the nicotinamidase from Arabidopsis thaliana (isoform 2)
SEQ ID No. 18: nucleotide sequence of the nicotinamidase from Arabidopsis thaliana (isoform 3)
SEQ ID No. 19: nucleotide sequence of the nicotinate phosphoribosyltransferase from Arabidopsis thaliana (isoform 1).
SEQ ID No. 20: nucleotide sequence of the nicotinate phosphoribosyltransferase from Arabidopsis thaliana (isoform 2).
SEQ ID No. 21: nucleotide sequence of the nicotinic acid mononucleotide adenyl transferase from Arabidopsis thaliana.
SEQ ID No. 22: nucleotide sequence of the NAD synthetase from Arabidopsis thaliana.

EXAMPLES

Example 1

Protocol for Measurement of Depth of Arabidopsis Root Growth in Growth Medium

Media
Germination medium: Half concentrated Murashige and Skoog salts; B5 vitamins; 1.5% sucrose; pH 5.8; 0.4% Difco agar.

Arabidopsis Plants
Sterilization of Arabidopsis seeds: 2 min. 70% ethanol; 10 min. bleach (6% active chlorine)+1 drop Tween 20 for 20 ml solution; wash 5 times with sterile tap water; sterilization is done in 2 ml eppendorf tubes. Arabidopsis seeds sink to the bottom of the tube, allowing removal of the liquids by means of a 1 ml pipetman.

Pregermination of seeds: In 9 cm Optilux Petridishes (Falcon) containing 10 ml sterile tap water. Low light overnight to 24 hours.

Growing of Arabidopsis plants: Seeds are sown in 25×150 mm glass tubes (Sigma C5916) with natural (transparent) colored closure (Sigma C5791) containing ±34 ml germination medium: 1 seed/tube. The tubes are put in the two outer rows of tube holders for 40 tubes (VWR nalg5970-0025) wrapped in aluminium foil so that the roots can grow in the dark. Plants are grown at 23° C. 30-50 µEinstein $s^{-1}m^{-2}$. 12 hours light-12 hours dark. (See FIG. 1)

Measuring Root Depth

After three weeks, the root depth is measured from the surface of the medium to the lowest point of root growth. (See FIG. 1).

Example 2

Analysis of Depth of Root Growth of Arabidopsis Plants Comprising a Transgene which Enhances Stress Tolerance Arabidopsis thaliana plants comprising a transgene encoding a dsRNA molecule which is capable of reducing the expression of endogenous PARP1 or PARP2 genes, as described in WO 00/04173 A1, (e.g. in Example 8 thereof) were grown as described in Example 1.

After three weeks, the depth of the roots of the transgenic plants was measured and compared to the depth of the roots of non-transgenic control plants or to non-transgenic isogenic plants grown in a similar manner.

In a first experiment, various populations of Arabidopsis thaliana cv. Col-0 plants comprising a transgene encoding a dsRNA molecule which is capable of reducing the expression of endogenous PARP2 genes (with lines 427-16 and 427-20 showing weak tolerance to high light stress and line 427-19 showing a moderate tolerance to high light stress) were compared with a population of non-transgenic Arabidopsis thaliana cv. Col-0 plants.

The results of the measurements were subjected to statistical analysis, summarized in Table 1, which also represents the mean, standard deviation and confidence intervals.

Figure 2:
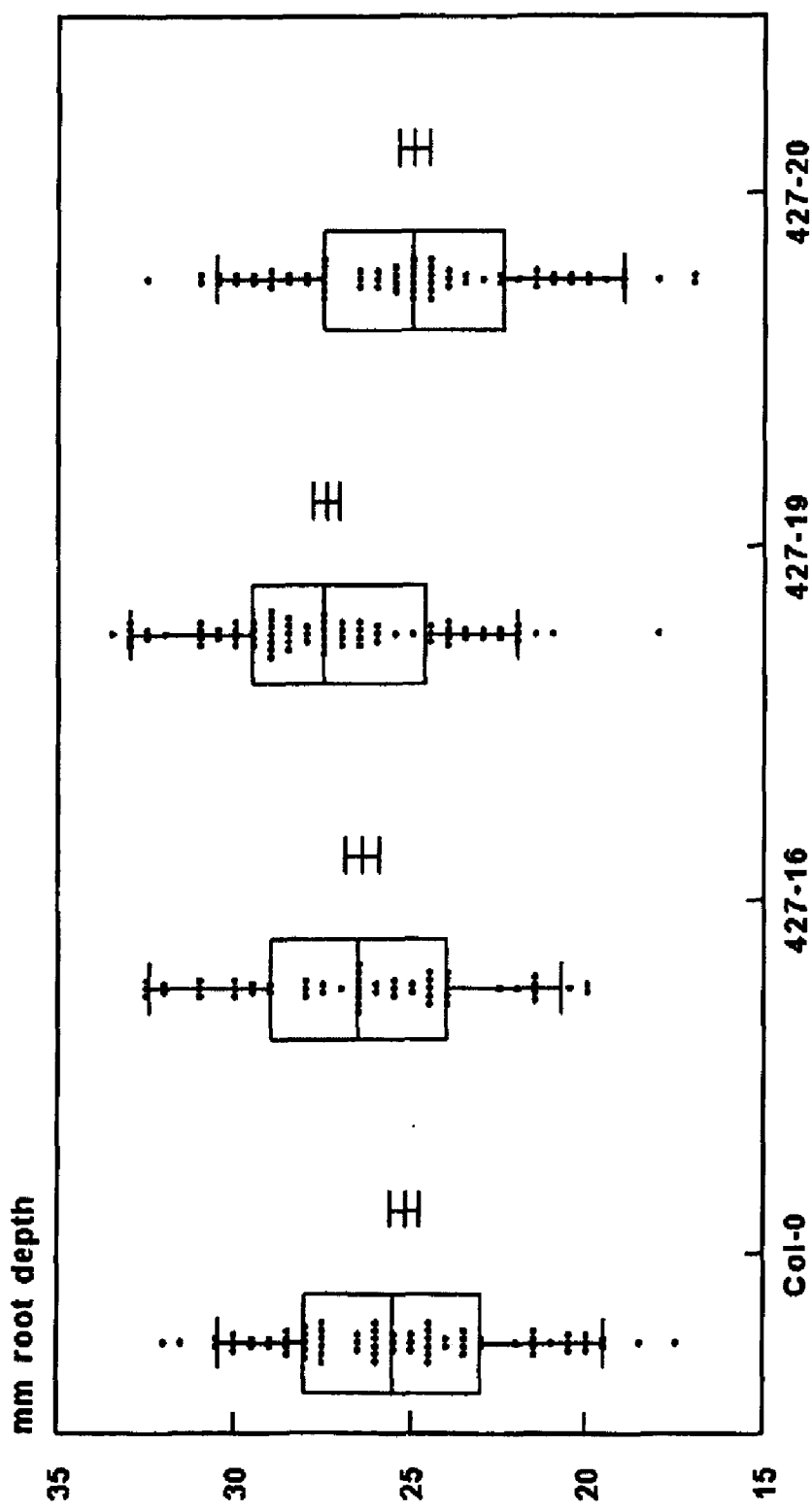
FIG. 2: Boxplot representation of the root depth (mm) of *Arabidopsis thaliana* cv. Col-0 plants comprising a transgene encoding a dsRNA molecule capable of reducing the expression of endogenous PARP2 genes compared to non-transgenic *Arabidopsis thaliana* plants (Col-0).

The roots of transgenic Arabidopsis thaliana plants with the highest tolerance to high light stress conditions (line 427-19) protruded statistically significant deeper (at 99% confidence level) into the growth medium than non-transgenic Arabidopsis thaliana cv. Col-0 control plants (see FIG. 2 and Table 1)

TABLE 1

Root depth (mm) of Arabidopsis thaliana cv. Col-0 plants comprising a transgene encoding a dsRNA molecule which is capable of reducing the expression of endogenous PARP2 genes as compared to non-transgenic Arabidopsis thaliana cv. Col-0 plants

|  | Col-0 | 427-16 | 427-19 | 427-20 |
|---|---|---|---|---|
| mean | 25.173611 | 26.388889 | 27.42 | 24.942029 |
| Standard dev. | 3.64166 | 3.422548 | 3.361185 | 3.69174 |
| Standard error | 0.429174 | 0.46575 | 0.388116 | 0.444433 |
| 95% Confidence | 0.858348 | 0.94128 | 0.776233 | 0.888866 |
| 99% Confidence | 1.141602 | 1.259388 | 1.032389* | 1.182192 |

*p < 0.01

In a further experiment, a population of transgenic Arabidopsis thaliana cv. Col-0 plants comprising a transgene encoding a dsRNA molecule which is capable of reducing the expression of endogenous PARP2 genes and which are tolerant to high light stress (line 427-22) were compared to a transgenic line containing a similar transgene but which was sensitive to high light stress (line 427-24), as well as to non-transgenic Arabidopsis thaliana cv. Col-0 control plants.

The results of the measurements were subjected to statistical analysis, summarized in Table 2, which also represents the mean, standard deviation and confidence intervals.

The roots of transgenic Arabidopsis thaliana cv. Col-0 plants of the stress tolerant transgenic line (line 427-22) protruded deeper into the growth medium (comprising 0.7% Difco agar instead of 0.4%) than the roots Arabidopsis thaliana cv. Col-0 control plants and than the roots of stress-sensitive transgenic Arabidopsis thaliana cv. Col-0 plant line (line 427-24) (see FIG. 3 and Table 2).

TABLE 2

Root depth (mm) of Arabidopsis thaliana cv. Col-0 plants comprising a transgene encoding a dsRNA molecule which is capable of reducing the expression of endogenous PARP2 genes as compared to non-transgenic Arabidopsis thaliana cv. Col-0 plants

|  | Col-0 | 427-22 | 427-24 |
|---|---|---|---|
| Mean | 18.291339 | 21.146154 | 17.384058 |
| Standard dev. | 2.928677 | 5.368981 | 2.740149 |
| Standard error | 0.259878 | 0.66594 | 0.329875 |
| 95% Confidence | 0.514558 | 1.33188 | 0.65975 |
| 99% Confidence | 0.680101 | 1.771401* | 0.877468 |

*p < 0.01

In another experiment, the following populations were analyzed:

C24: wild-type Arabidopsis line; line 1599: A. thaliana transgenic line comprising anti-PARP2 transgene with a high tolerance to high light stress conditions; line 1463: A. thaliana transgenic line comprising anti-PARP2 transgene with a moderate tolerance to high light stress conditions; line 1681: A. thaliana transgenic line comprising anti-PARP 1 gene with a moderate tolerance to high light stress conditions; and line 1690: A. thaliana transgenic line comprising anti-PARP1 gene with a moderate tolerance to high light stress conditions. The stress tolerance of line 1599 is very high, the stress tolerance of lines 1463, 1681 and 1690 varies from moderate to high.

The results of the measurements were subjected to statistical analysis, summarized in Table 3, which represents the mean, standard deviation and confidence intervals.

The roots of transgenic Arabidopsis thaliana cv. C24 plants comprising a transgene encoding a dsRNA molecule which is capable of reducing the expression of endogenous PARP1 genes (lines 1681 and 1690) or PARP2 genes (lines 1599 and 1463) protruded deeper in the growth medium than the non-transgenic Arabidopsis thaliana cv. C24 control plants (see FIG. 4 and Table 3)

TABLE 3

Root depth (mm) of Arabidopsis thaliana cv. C24 plants comprising a transgene encoding a dsRNA molecule which is capable of reducing the expression of endogenous PARP1 or PARP2 genes as compared to non-transgenic Arabidopsis thaliana cv. C24 plants

|  | C24 | 1599 | 1463 | 1681 | 1690 |
|---|---|---|---|---|---|
| mean | 16.18 | 18.125 | 17.405063 | 17.433333 | 17.897727 |
| Standard dev. | 2.192181 | 2.992481 | 2.16036 | 2.112246 | 1.885007 |
| Standard error | 0.219218 | 0.451133 | 0.243059 | 0.27269 | 0.284175 |

TABLE 3-continued

Root depth (mm) of *Arabidopsis thaliana* cv. C24 plants comprising a transgene encoding a dsRNA molecule which is capable of reducing the expression of endogenous PARP1 or PARP2 genes as compared to non-transgenic *Arabidopsis thaliana* cv. C24 plants

|  | C24 | 1599 | 1463 | 1681 | 1690 |
|---|---|---|---|---|---|
| 95% Confidence | 0.438436 | 0.911741 | 0.486119 | 0.551106 | 0.574319 |
| 99% Confidence | 0.58312 | 1.219865* | 0.646538* | 0.737353* | 0.76841* |

*$p < 0.01$

In a further experiment, a 1:1 segregating population of transgenic *Arabidopsis thaliana* cv. Col-0 line comprising a transgene encoding a dsRNA molecule which is capable of reducing the expression of endogenous PARP2 genes and with high tolerance to high light stress, was analyzed. The presence of the transgene was verified by PCR analysis.

Plants comprising the transgene had roots which protruded deeper into the growth medium than the azygous *Arabidopsis thaliana* cv. Col-0 plants derived from line 427-19 (see FIG. 5 and Table 4)

TABLE 4

Root depth (mm) of *Arabidopsis thaliana* cv. Col-0 plants comprising a transgene encoding a dsRNA molecule which is capable of reducing the expression of endogenous PARP2 genes as compared to the azygous *Arabidopsis thaliana* cv. Col-0 plants

|  | Azygous 427-19 | Transgenic 427-19 |
|---|---|---|
| Mean | 25.296512 | 27.38172 |
| Standard dev. | 3.573907 | 3.244894 |
| Standard error | 0.385384 | 0.33648 |
| 95% Confidence | 0.770769 | 0.67296 |
| 99% Confidence | 1.025122 | 0.895036* |

*$p < 0.01$

Example 3

Analysis of Depth of Root Growth of *Arabidopsis* Plants after Application of Imidacloprid

*Arabidopsis thaliana* cv. C24 plants were grown as described in Example 1 on germination medium (with 0.7% Difco agar in stead of 0.4%) comprising various concentrations of imidacloprid (0, 50, and 100 mg/l). After three weeks, the depth of the roots of the plants treated with 50 and 100 mg/l imidacloprid was measured and compared to the depth of the roots of untreated plants grown in a similar manner.

Figure 6:
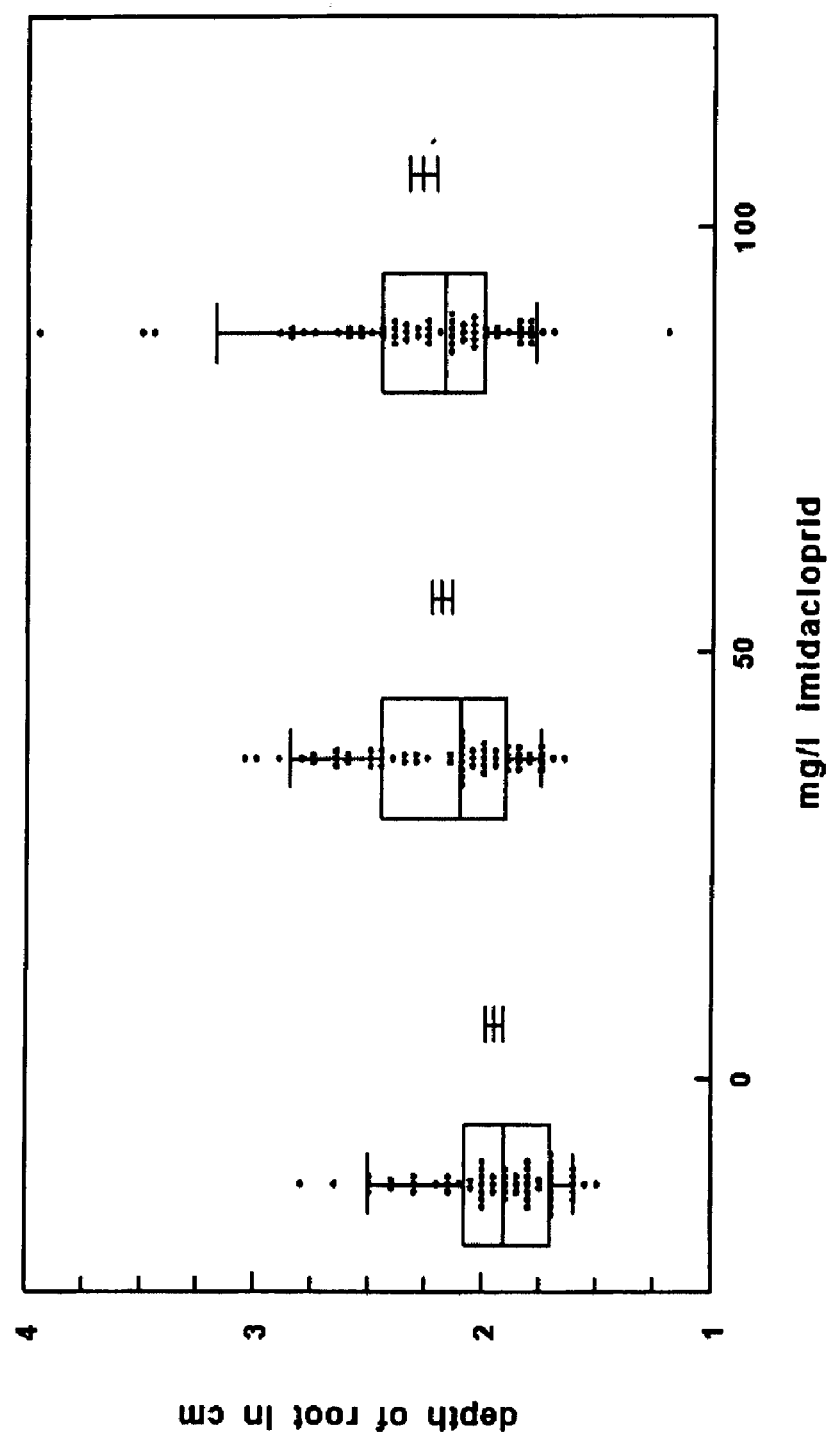

The roots of the treated *Arabidopsis* plants protruded deeper in the growth medium than the roots of the non-treated *Arabidopsis* plants (see FIG. 6 and Table 5)

TABLE 5

Root depth (mm) of *Arabidopsis thaliana* cv. C24 plants treated with 50 and 100 mg/l imidacloprid as compared to *Arabidopsis thaliana* cv. C24 plants not treated with imidacloprid

|  | 0 mg/L | 50 mg/L | 100 mg/L |
|---|---|---|---|
| Mean | 1.9475 | 2.1875 | 2.2725 |
| Standard dev. | 0.289714 | 0.353508 | 0.456072 |
| Standard error | 0.037402 | 0.045638 | 0.058879 |
| 95% Confidence | 0.075589 | 0.092234 | 0.118994 |
| 99% Confidence | 0.101135 | 0.123404* | 0.159208* |

*$p < 0.01$

Example 4

Analysis of Depth of Root Growth of *Arabidopsis* Plants after Application of 6-Chloronicotinic Acid (6-CNA)

*Arabidopsis thaliana* cv. C24 plants were grown as described in Example 1 on germination medium comprising various concentrations of 6-CNA (0, 1, and 5 mg/l). After three weeks, the depth of the roots of the plants treated with 1 and 5 mg/l 6-CNA was measured and compared to the depth of the roots of the plants not treated with 6-CNA grown in a similar manner.

The roots of the treated *Arabidopsis* plants protruded deeper in the growth medium than the roots of the non-treated *Arabidopsis* plants (see FIG. 7 and Table 6)

TABLE 6

Root depth (mm) of *Arabidopsis thaliana* cv. C24 plants treated with 1 and 5 mg/l 6-CNA as compared to *Arabidopsis thaliana* cv. Col-0 plants not treated with 6-CNA

|  | 0 mg/L | 1 mg/L | 5 mg/L |
|---|---|---|---|
| Mean | 2.031034 | 2.179661 | 2.118367 |
| Standard dev. | 0.189373 | 0.186418 | 0.237762 |
| Standard error | 0.024866 | 0.02427 | 0.033966 |
| 95% Confidence | 0.050254 | 0.049049 | 0.068645** |
| 99% Confidence | 0.067237 | 0.065625* | 0.091844 |

*$p < 0.01$
**$p < 0.05$

The invention claimed is:

1. A method for increasing the tolerance of a plant cell or plant to hypoxic or anoxic conditions, comprising:
   a) applying an effective amount of a compound of formula (I)

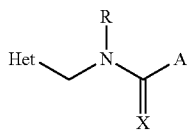

wherein
Het represents a heterocycle which is either mono- or polysubstituted by fluorine, chlorine, methyl or ethyl, wherein said heterocycle is:
pyrid-3-yl, pyrid-5-yl, 3-pyridinio, 1-oxido-5-pyridinio, 1-oxido-5-pyridinio, tetra-hydrofuran-3-yl, or thiazol-5-yl,
A represents $C_1$-$C_6$-alkyl, —N($R^1$)($R^2$) or S($R^2$),
in which
$R^1$ represents hydrogen, $C_1$-$C_6$-alkyl, phenyl-$C_1$-$C_4$-alkyl, $C_3$-$C_6$-cycloalkyl, $C_2$-$C_6$-alkenyl or $C_2$-$C_6$-alkynyl, and
$R^2$ represents $C_1$-$C_6$-alkyl, $C_2$-$C_6$-alkenyl, $C_2$-$C_6$-alkynyl, —C(=O)—$CH_3$ or benzyl,
R represents hydrogen, $C_1$-$C_6$-alkyl, $C_2$-$C_6$-alkenyl, $C_2$-$C_6$-alkynyl, —C(=O)—$CH_3$ or benzyl or together with $R^2$ represents the groups below:
—$CH_2$—$CH_2$—, $CH_2$—$CH_2$—$CH_2$—, —$CH_2$—O—$CH_2$—, —$CH_2$—S—$CH_2$—, —$CH_2$—NH—$CH_2$—, —$CH_2$—N($CH_3$)—$CH_2$—, and
X represents N—$NO_2$, N—CN or CH—$NO_2$
on said plant cell or plant or on its locus, or on seeds of said plant; and
   b) identifying a plant or plant cell which has an increased tolerance to hypoxic or anoxic conditions compared to a plant cell or plant where said compound was not applied to the plant, its locus or its seeds.

2. A method for increasing the penetrance of roots of a plant into a growth medium, comprising:
   a) applying an effective amount of a compound of formula (I)

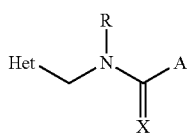

wherein
Het represents a heterocycle which is either mono- or polysubstituted by fluorine, chlorine, methyl or ethyl, wherein said heterocycle is:
pyrid-3-yl, pyrid-5-yl, 3-pyridinio, 1-oxido-5-pyridinio, 1-oxido-5-pyridinio, tetra-hydrofuran-3-yl, or thiazol-5-yl,
A represents $C_1$-$C_6$-alkyl, —N($R^1$)($R^2$) or S($R^2$),
in which
$R^1$ represents hydrogen, $C_1$-$C_6$-alkyl, phenyl-$C_1$-$C_4$-alkyl, $C_3$-$C_6$-cycloalkyl, $C_2$-$C_6$-alkenyl or $C_2$-$C_6$-alkynyl, and
$R^2$ represents $C_1$-$C_6$-alkyl, $C_2$-$C_6$-alkenyl, $C_2$-$C_6$-alkynyl, —C(=O)—$CH_3$ or benzyl,
R represents hydrogen, $C_1$-$C_6$-alkyl, $C_2$-$C_6$-alkenyl, $C_2$-$C_6$-alkynyl, —C(=O)—$CH_3$ or benzyl or together with $R^2$ represents the groups below:
—$CH_2$—$CH_2$—, —$CH_2$—$CH_2$—$CH_2$—, —$CH_2$—O—$CH_2$—, —$CH_2$—S—$CH_2$—, —$CH_2$—NH—$CH_2$—, —$CH_2$—N($CH_3$)—$CH_2$—, and
X represents N—$NO_2$, N—CN or CH—$NO_2$
on said plant or on its locus, or on seeds of said plant; and
   b) identifying a plant which has an increased penetrance of roots into a growth medium compared to a plant where said compound was not applied to the plant, its locus or its seeds.

3. The method of claim 1 or 2, wherein said compound of formula (I) is a neonicotinoid compound.

4. The method of claim 1 or 2, wherein said heterocycle represented by Het of said compound of formula (I) is a pyrid-3-yl heterocycle substituted by chlorine.

5. The method of claim 4, wherein said compound of formula (I) is imidacloprid, or thiacloprid.

6. A method for increasing the tolerance of a plant to hypoxic or anoxic conditions, comprising the step of: providing said plant with an effective amount of 6-chloronicotinic acid, whereby said 6-chloronicotinic acid is applied directly to said plant or the habitat thereof, or said plant's seed, and the tolerance of said plant to hypoxic or anoxic conditions is increased.

7. A method for increasing the penetrance of roots of a plant into a growth medium comprising the step of: providing said plant with an effective amount of 6-chloronicotinic acid, whereby said 6-chloronicotinic acid is applied directly to said plant or the habitat thereof, or said plant's seed, and the penetrance of roots of said plant into a growth medium is increased.

8. The method of claim 1 or 2, wherein said compound is applied to said plant, said locus, or said seeds when planting said plant or seed.

* * * * *

SEQUENCE LISTING

```
<160> NUMBER OF SEQ ID NOS: 22

<210> SEQ ID NO 1
<211> LENGTH: 3187
<212> TYPE: DNA
<213> ORGANISM: Artificial Sequence
<220> FEATURE:
<223> OTHER INFORMATION: parp1 coding region from Arabidopsis thaliana
<220> FEATURE:
```

<221> NAME/KEY: misc_feature
<222> LOCATION: (11)..(2962)
<223> OTHER INFORMATION: open reading frame

<400> SEQUENCE: 1

| | | | | | |
|---|---|---|---|---|---|
| taccggagaa | atggcaagcc | cacataagcc | gtggagggcg | gagtatgcaa | agtcgtcgag | 60 |
| gtcttcatgt | aaaacttgca | agtccgtcat | taacaaggag | aactttcgtc | ttggaaagtt | 120 |
| ggttcaatct | actcacttcg | atggcatcat | gcccatgtgg | aaccatgctt | cttgtatact | 180 |
| gaagaagacg | aagcagataa | aatcagttga | tgatgttgaa | ggcatagaat | cacttcgttg | 240 |
| ggaagatcag | caaagatta | gaaaatatgt | cgaatctgga | gcagggagta | acacaagcac | 300 |
| aagcacaggc | acaagcacga | gcagtaccgc | taataatgcc | aaactagaat | atgggattga | 360 |
| agtgtcacaa | acttcccgtg | ccggttgcag | aaagtgtagc | gaaaagatct | tgaaaggaga | 420 |
| ggtacgtata | ttctccaagc | ctgaaggccc | gggtaacaaa | ggtttgatgt | ggcatcacgc | 480 |
| taaatgtttc | cttgaaatgt | cttcctctac | tgaactggaa | agtttgtctg | atggagaag | 540 |
| tataccagac | tcagaccaag | aagctcttct | tcccttagtg | aagaaagctc | tgccggcagc | 600 |
| caaaactgag | acagcagaag | cacgtcaaac | aaattcaaga | gcaggcacaa | aacgaaaaaa | 660 |
| tgattctgtt | gataacgaga | agtcgaaact | agcaaaaagt | agttttgaca | tgtctacaag | 720 |
| tggtgcttta | caaccttgta | gcaaagaaaa | ggaaatggag | gcccaaacta | aggaattgtg | 780 |
| ggacctgaag | gatgatctga | aaaaatatgt | aacatcagct | gagttgcggg | aaatgcttga | 840 |
| agtaaatgaa | caaagtacaa | gaggatctga | acttgatctg | cgtgataaat | gtgctgatgg | 900 |
| catgatgttt | ggcccactcg | ctctctgccc | aatgtgctct | gggcatcttt | ctttctccgg | 960 |
| aggactttac | cgatgccatg | gatacatctc | agaatggagc | aaatgttctc | attccacttt | 1020 |
| ggatccagac | cgcatcaaag | ggaagtggaa | aatccctgac | gaaacagaaa | atcaattcct | 1080 |
| tctgaagtgg | aataagtctc | aaaagagtgt | gaagccaaaa | cgtattctgc | gtcctgtatt | 1140 |
| gtctggcgag | acatctcagg | gtcaaggttc | taaagatgca | actgactcct | caaggagtga | 1200 |
| aaggctagca | gatcttaaag | tttcaattgc | tggaaatact | aaggaaaggc | aaccatggaa | 1260 |
| gaagagaatt | gaggaagctg | gtgcagagtt | tcatgctaat | gttaaaaaag | gtacaagctg | 1320 |
| tttggttgtt | tgtggactga | cagatatcag | agacgctgaa | atgagaaagg | caaggaggat | 1380 |
| gaaagtggca | atcgtgagag | aggattattt | ggttgattgt | tttaaaaaac | agaggaaact | 1440 |
| tccatttgac | aagtacaaaa | ttgaagacac | tagtgagagc | cttgtcactg | ttaaagtaaa | 1500 |
| aggacgaagc | gctgtgcatg | aagcgtctgg | cctccaagag | cactgtcaca | ttcttgaaga | 1560 |
| tgggaacagt | atctataaca | caactctgag | catgtctgat | ctctctaccg | gtatcaatag | 1620 |
| ttattacata | ctccagataa | tccaagaaga | taaaggttca | gattgttacg | tatttcgtaa | 1680 |
| atggggccga | gttggaaatg | aaaagattgg | tggtaacaaa | gtggaggaaa | tgtcaaagtc | 1740 |
| tgatgcggtt | cacgaattca | aacgtctatt | tcttgaaaaa | accggaaaca | catgggaatc | 1800 |
| ttgggaacaa | aaaacgaatt | ccagaaaaca | acctggaaaa | tttctcccgt | tggacattga | 1860 |
| ttatggagtt | aataagcaag | tagccaaaaa | agagccattt | cagaccagta | gcaaccttgc | 1920 |
| tccatcatta | atagaattga | tgaagatgct | ttttgatgtg | gaaacttaca | gatctgcaat | 1980 |
| gatggagttc | gagataaata | tgtcagagat | gccacttggg | aagctcagca | aacataatat | 2040 |
| acagaagggt | tttgaggcat | tgacggagat | acagaggcta | ttgactgaaa | gcgaccccca | 2100 |
| gcctactatg | aaagaaagct | tgcttgttga | tgctagtaac | agatttttta | ccatgatccc | 2160 |
| ttctattcat | cctcatatta | tccgagatga | agatgacttt | aagtcaaagg | tgaaaatgct | 2220 |

-continued

```
cgaggctctg caggatatcg aaatagcttc aagaatagtt ggctttgatg ttgatagcac    2280
cgaatctctt gatgataagt ataagaagct gcattgcgat atctcaccac ttcctcatga    2340
tagcgaagat tatcgattaa tcgagaagta tcttaacaca actcatgccc caacgcatac    2400
agagtggagt cttgagctag aggaagtttt tgctcttgaa agagaaggag agtttgataa    2460
atatgctccc cacagagaaa aacttggcaa taagatgctc ctatggcatg gttctcgatt    2520
aacgaatttt gttggaatat tgaaccaagg actgagaatt gcacctccag aagctcctgc    2580
tactggttac atgtttggaa aagggatata ctttgctgac cttgtcagta aaagtgctca    2640
gtactgctac acttgtaaga aaaatccggt gggtctaatg cttctgagtg aagttgcatt    2700
gggagaaata catgagctaa caaaagctaa gtatatggat aaacctccga gagggaaaca    2760
ctcgaccaaa gggctcggca agaaagtgcc tcaagattcc gagtttgcca agtggagagg    2820
tgatgtgact gttccctgtg gaaaacctgt ttcatcaaag gtcaaggctt ctgagcttat    2880
gtacaatgag tatatcgtct acgatacagc ccaggtgaag ttgcagttct tgttgaaagt    2940
aaggtttaag cacaagagat gagcctgaac caaacaagaa gacgtcactt ctgttaacta    3000
aatgtttttt tgggaaatcg aatccaacac gaagacttaa cttttgtaac taaattgctt    3060
ttgataaatt gaattcaaca tgtagtcaca gatttaactc tctggcgttg tagatgtttc    3120
tggttttaaa agagcgtact ctacattttg ttatgctttt tctcagtaat gacacttctt    3180
aagactt                                                             3187
```

<210> SEQ ID NO 2
<211> LENGTH: 2147
<212> TYPE: DNA
<213> ORGANISM: Artificial Sequence
<220> FEATURE:
<223> OTHER INFORMATION: parp2 coding region from Arabidopsis thaliana
<220> FEATURE:
<221> NAME/KEY: misc_feature
<222> LOCATION: (129)..(2042)
<223> OTHER INFORMATION: open reading frame

<400> SEQUENCE: 2

```
attgatgaag aagaaaacga agaagaagac tcttcaaatg ctcgcgcgaa ctcacttctg     60
acgaaaacca tacttcctca gtctcattcc cttttccgacg aactattctc ctgaagaaga   120
agacgaaaat ggcgaacaag ctcaaagtcg acgaactccg tttaaaactc gccgagcgtg    180
gactcagtac tactggagtc aaagccgttc tggtggagag gcttgaagag gctatcgcag    240
aagacactaa gaaggaagaa tcaaagagca agaggaaaag aaattcttct aatgatactt    300
atgaatcgaa caaattgatt gcaattggcg aatttcgtgg gatgattgtg aaggaattgc    360
gtgaggaagc tattaagaga ggcttagata acaggaac caaaaaggat cttcttgaga     420
ggctttgcaa tgatgctaat aacgtttcca atgcaccagt caaatccagt aatgggacag    480
atgaagctga agatgacaac aatggctttg aagaagaaaa gaaagaagag aaaatcgtaa    540
ccgcgacaaa gaagggtgca gcggtgctag atcagtggat tcctgatgag ataaagagtc    600
agtaccatgt tctacaaagg ggtgatgatg tttatgatgc tatcttaaat cagacaaatg    660
tcagggataa taataacaag ttcttttgtcc tacaagtcct agagtcggat agtaaaaaga    720
catacatggt ttacactaga tggggaagag ttggtgtgaa aggacaaagt aagctagatg    780
ggccttatga ctcatgggat cgtgcgatag agatatttac caataagttc aatgacaaga    840
caaagaatta ttggtctgac agaaaggagt ttatcccaca tcccaagtcc tatacatggc    900
tcgaaatgga ttacggaaaa gaggaaaatg attcaccggt caataatgat attccgagtt    960
```

| catcttccga agttaaacct gaacaatcaa aactagatac tcgggttgcc aagttcatct | 1020 |
| ctcttatatg taatgtcagc atgatggcac agcatatgat ggaaatagga tataacgcta | 1080 |
| acaaattgcc actcggcaag ataagcaagt ccacaatttc aaagggttat gaagtgctga | 1140 |
| agagaatatc ggaggtgatt gaccggtatg atagaacgag gcttgaggaa ctgagtggag | 1200 |
| agttctacac agtgatacct catgattttg gttttaagaa aatgagtcag tttgttatag | 1260 |
| acactcctca aaagttgaaa cagaaaattg aaatggttga agcattaggt gaaattgaac | 1320 |
| tcgcaacaaa gttgttgtcc gtcgacccgg gattgcagga tgatccttta tattatcact | 1380 |
| accagcaact taattgtggt ttgacgccag taggaaatga ttcagaggag ttctctatgg | 1440 |
| ttgctaatta catggagaac actcatgcaa agacgcattc gggatatacg gttgagattg | 1500 |
| cccaactatt tagagcttcg agagctgttg aagctgatcg attccaacag ttttcaagtt | 1560 |
| cgaagaacag gatgctactc tggcacggtt cacgtctcac taactgggct ggtattttat | 1620 |
| ctcaaggtct gcgaatagct cctcctgaag cgcctgtaac tggttacatg tttggaaaag | 1680 |
| gggtttactt tgcggatatg ttctccaaga gtgcgaacta ttgctatgcc aacactggcg | 1740 |
| ctaatgatgg cgttctgctc ctctgcgagg ttgctttggg agacatgaat gaacttctgt | 1800 |
| attcagatta taacgcggat aatctacccc cgggaaagct aagcacaaaa ggtgtgggga | 1860 |
| aaacagcacc aaacccatca gaggctcaaa cactagaaga cggtgttgtt gttccacttg | 1920 |
| gcaaaccagt ggaacgttca tgctccaagg ggatgttgtt gtacaacgaa tatatagtct | 1980 |
| acaatgtgga acaaatcaag atgcgttatg tgatccaagt caaattcaac tacaagcact | 2040 |
| aaaacttatg tatattagct tttgaacatc aactaattat ccaaaaatca gcgttttatt | 2100 |
| gtatttcttt caaactcctt catctctgat tttgcacggt tcactcg | 2147 |

<210> SEQ ID NO 3
<211> LENGTH: 3211
<212> TYPE: DNA
<213> ORGANISM: Artificial Sequence
<220> FEATURE:
<223> OTHER INFORMATION: parp1 coding region 1 from Zea mays
<220> FEATURE:
<221> NAME/KEY: misc_feature
<222> LOCATION: (113)..(3022)
<223> OTHER INFORMATION: open reading frame

<400> SEQUENCE: 3

| acctacctga atacgtcatc cctaagtgtt ccgcttcctc tgtcgtccgg cctccaactc | 60 |
| catcgaaggg gctagggaga ggagggaacc cgaaccacag caggccggcg caatggcggc | 120 |
| gccgccaaag gcgtggaagg cggagtatgc caagtctggg cgggcctcgt gcaagtcatg | 180 |
| ccggtcccct atcgccaagg accagctccg tcttggcaag atggttcagg cgtcacagtt | 240 |
| cgacggcttc atgccgatgt ggaaccatgc cagcgttgac gatgttgaag ggatagatgc | 300 |
| acttagatgg gatgatcaag agaagatacg aaactacgtt gggagtgcct cagctggtac | 360 |
| aagttctaca gctgctcctc ctgagaaatg tacaattgag attgctccat ctgcccgtac | 420 |
| ttcatgtaga cgatgcagtg aaaagattac aaaaggatcg gtccgtcttt cagctaagct | 480 |
| tgagagtgaa ggtcccaagg gtataccatg gtatcatgcc aactgtttct ttgaggtatc | 540 |
| cccgtctgca actgttgaga agttctcagg ctgggatact ttgtccgatg aggataagag | 600 |
| aaccatgctc gatcttgtta aaaagatgt tggcaacaat gaacaaaata gggttccaa | 660 |
| gcgcaagaaa agtgaaaatg atattgtatag ctacaaatcc gccaggttag atgaaagtac | 720 |
| atctgaaggt acagtgcgaa acaaagggca acttgtagac ccacgtggtt ccaatactag | 780 |

-continued

```
ttcagctgat atccaactaa agcttaagga gcaaagtgac acactttgga agttaaagga   840
tggacttaag actcatgtat cggctgctga attaagggga atgcttgagg ctaatgggca   900
ggatacatca ggaccagaaa ggcacctatt ggatcgctgt gcggatggaa tgatatttgg   960
agcgctgggt ccttgcccag tctgtgctaa tggcatgtac tattataatg gtcagtacca  1020
atgcagtggt aatgtgtcag agtggtccaa gtgtacatac tctgccacag aacctgtccg  1080
cgttaagaag aagtggcaaa ttccacatgg aacaaagaat gattaccctta tgaagtggtt  1140 caaatctcaa aaggttaaga accagagag ggttcttcca ccaatgtcac ctgagaaatc  1200
tggaagtaaa gcaactcaga gaacatcatt gctgtcttct aaagggttgg ataaattaag  1260
gttttctgtt gtaggacaat caaaagaagc agcaaatgag tggattgaga agctcaaact  1320
tgctggtgcc aacttctatg ccagggttgt caaagatatt gattgtttaa ttgcatgtgg  1380
tgagctcgac aatgaaaatg ctgaagtcag gaaagcaagg aggctgaaga taccaattgt  1440
aagggagggt tacattggag aatgtgttaa aagaacaaa atgctgccat ttgatttgta  1500
taaactagag aatgccttag agtcctcaaa aggcagtact gtcactgtta aagttaaggg  1560
ccgaagtgct gttcatgagt cctctggttt gcaagatact gctcacattc ttgaagatgg  1620
gaaaagcata tacaatgcaa ccttaaacat gtctgacctg cactaggtg tgaacagcta  1680 ctatgtactc cagatcattg aacaggatga tgggtctgag tgctacgtat ttcgtaagtg  1740
gggacgggtt gggagtgaga aaattggagg gcaaaaactg gaggagatgt caaaaactga  1800
ggcaatcaag gaattcaaaa gattatttct tgagaagact ggaaactcat gggaagcttg  1860
ggaatgtaaa accaattttc ggaagcagcc tgggagattt tacccacttg atgttgatta  1920
tggtgttaag aaagcaccaa aacggaaaga tatcagtgaa atgaaaagtt ctcttgctcc  1980
tcaattgcta gaactcatga agatgctttt caatgtggag acatatagag ctgctatgat  2040
ggaatttgaa attaatatgt cagaaatgcc tcttgggaag ctaagcaagg aaaatattga  2100
gaaaggattt gaagcattaa ctgagataca gaatttattg aaggacaccg ctgatcaagc  2160
actggctgtt agagaaagct taattgttgc tgcgagcaat cgcttttca ctcttatccc  2220 ttctattcat cctcatatta tacgggatga ggatgatttg atgatcaaag cgaaaatgct  2280
tgaagctctg caggatattg aaattgcttc aaagatagtt ggcttcgata gcgacagtga  2340
tgaatctctt gatgataaat atatgaaact tcactgtgac atcacccgc tggctcacga  2400 tagtgaagat tacaagttaa ttgagcagta tctcctcaac acacatgctc ctactcacaa  2460
ggactggtcg ctggaactgg aggaagtttt ttcacttgat cgagatggag aacttaataa  2520
gtactcaaga tataaaaata atctgcataa caagatgcta ttatggcacg gttcaaggtt  2580
gacgaatttt gtgggaattc ttagtcaagg gctaagaatt gcacctcctg aggcacctgt  2640
tactggctat atgttcggca aaggcctcta cttttgcagat ctagtaagca agagcgcaca  2700
atactgttat gtggatagga ataatcctgt aggtttgatg cttctttctg aggttgcttt  2760
aggagacatg tatgaactaa agaaagccac gtccatggac aaacctccaa gagggaagca  2820
ttcgaccaag ggattaggca aaaccgtgcc actggagtca gagtttgtga agtgaggga  2880 tgatgtcgta gttccctgcg gcaagccggt gccatcatca attaggagct ctgaactcat  2940
gtacaatgag tacatcgtct acaacacatc ccaggtgaag atgcagttct tgctgaaggt  3000
gcgtttccat cacaagaggt agctgggaga ctaggcaagt agagttggaa ggtagagaag  3060
cagagttagg cgatgcctct tttggtatta ttagtaagcc tggcatgtat ttatgggtgc  3120
tcgcgcttga tccattttgg taagtgttgc ttgggcatca gcgcgaatag caccaatcac  3180
``` acactttac ctaatgacgt tttactgtat a                                    3211

<210> SEQ ID NO 4
<211> LENGTH: 3212
<212> TYPE: DNA
<213> ORGANISM: Artificial Sequence
<220> FEATURE:
<223> OTHER INFORMATION: parp1 coding region 2 from Zea mays
<220> FEATURE:
<221> NAME/KEY: misc_feature
<222> LOCATION: (81)..(3020)
<223> OTHER INFORMATION: open reading frame

<400> SEQUENCE: 4

```
gcttcctctg tcgtccggcc tccaactcca tcgaaggggc tagggagagg agggaacccg      60
aaccacagca ggccggcgca atggcggcgc cgccaaaggc gtggaaggcg agtatgcca     120
agtctgggcg ggcctcgtgc aagtcatgcc ggtcccctat cgccaaggac cagctccgtc     180
ttggcaagat ggttcaggcg tcacagttcg acggcttcat gccgatgtgg aaccatgcca     240
ggtgcatctt cagcaagaag aaccagataa atccgttga cgatgttgaa gggatagatg     300
cacttagatg ggatgatcaa gagaagatac gaaactacgt tgggagtgcc tcagctggta     360
caagttctac agctgctcct cctgagaaat gtacaattga gattgctcca tctgcccgta     420
cttcatgtag acgatgcagt gaaaagatta caaaaggatc ggtccgtctt tcagctaagc     480
ttgagagtga aggtcccaag ggtataccat ggtatcatgc aactgtttc tttgaggtat     540
ccccgtctgc aactgttgag aagttctcag gctgggatac tttgtccgat gaggataaga     600
gaaccatgct cgatcttgtt aaaaaagatg ttggcaacaa tgaacaaaat aagggttcca     660
agcgcaagaa aagtgaaaat gatattgata gctacaaatc cgccaggtta gatgaaagta     720
catctgaagg tacagtgcga acaaagggc aacttgtaga cccacgtggt tccaatacta     780
gttcagctga tatccaacta aagcttaagg agcaaagtga cacactttgg aagttaaagg     840
atggacttaa gactcatgta tcggctgctg aattaaggga tatgcttgag ctaatgggc     900
aggatacatc aggaccagaa aggcacctat ggatcgctg tgcggatgga atgatatttg     960
gagcgctggg tccttgccca gtctgtgcta atggcatgta ctattataat ggtcagtacc    1020
aatgcagtgg taatgtgtca gagtggtcca agtgtacata ctctgccaca gaacctgtcc    1080
gcgttaagaa gaagtggcaa attccacatg gaacaaagaa tgattacctt atgaagtggt    1140
tcaaatctca aaaggttaag aaaccagaga gggttcttcc accaatgtca cctgagaaat    1200
ctggaagtaa agcaactcag agaacatcat tgctgtcttc taaagggttg gataaattaa    1260
ggttttctgt tgtaggacaa tcaaaagaag cagcaaatga gtggattgag aagctcaaac    1320
ttgctggtgc caacttctat gccagggttg tcaaagatat tgattgttta attgcatgtg    1380
gtgagctcga caatgaaaat gctgaagtca ggaaagcaag gaggctgaag ataccaattg    1440
taagggaggg ttacattgga gaatgtgtta aaaagaacaa aatgctgcca tttgatttgt    1500
ataaactaga gaatgcctta gagtcctcaa aaggcagtac tgtcactgtt aaagttaagg    1560
gccgaagtgc tgttcatgag tcctctggtt gcaagatac tgctcacatt cttgaagatg    1620
ggaaaagcat atacaatgca accttaaaca tgtctgacct ggcactaggt gtgaacagct    1680
actatgtact ccagatcatt gaacaggatg atgggtctga gtgctacgta tttcgtaagt    1740
ggggacgggt tgggagtgag aaaattggag gcaaaaact ggaggagatg tcaaaaactg    1800
aggcaatcaa ggaattcaaa agattatttc ttgagaagac tggaaactca tgggaagctt    1860
gggaatgtaa aaccaatttt cggaagcagc ctgggagatt ttacccactt gatgttgatt    1920
```

```
atggtgttaa gaaagcacca aaacggaaag atatcagtga aatgaaaagt tctcttgctc    1980
ctcaattgct agaactcatg aagatgcttt tcaatgtgga gacatataga gctgctatga    2040
tggaatttga aattaatatg tcagaaatgc ctcttgggaa gctaagcaag gaaaatattg    2100
agaaaggatt tgaagcatta actgagatac agaatttatt gaaggacacc gctgatcaag    2160
cactggctgt tagagaaagc ttaattgttg ctgcgagcaa tcgcttttc actcttatcc     2220
cttctattca tcctcatatt atacgggatg aggatgattt gatgatcaaa gcgaaaatgc    2280
ttgaagctct gcaggatatt gaaattgctt caaagatagt tggcttcgat agcgacagtg    2340
atgaatctct tgatgataaa tatatgaaac ttcactgtga catcaccccg ctggctcacg    2400
atagtgaaga ttacaagtta attgagcagt atctcctcaa cacacatgct cctactcaca    2460
aggactggtc gctggaactg gaggaagttt tttcacttga tcgagatgga gaacttaata    2520
agtactcaag atataaaaat aatctgcata acaagatgct attatggcac ggttcaaggt    2580
tgacgaattt tgtgggaatt cttagtcaag ggctaagaat tgcacctcct gaggcacctg    2640
ttactggcta tatgttcggc aaaggcctct actttgcaga tctagtaagc aagagcgcac    2700
aatactgtta tgtggatagg aataatcctg taggtttgat gcttctttct gaggttgctt    2760
taggagacat gtatgaacta agaaaagcca cgtccatgga caaacctcca agagggaagc    2820
attcgaccaa gggattaggc aaaaccgtgc cactggagtc agagtttgtg aagtggaggg    2880
atgatgtcgt agttccctgc ggcaagccgg tgccatcatc aattaggagc ctgaactca    2940
tgtacaatga gtacatcgtc tacaaacaca tcccaggtgaa gatgcagttc ttgctgaagg    3000
tgcgttttcca tcacaagagg tagctgggag actaggcaag tagagttgga aggtagagaa    3060
gcagagttag gcgatgcctc ttttggtatt attagtaagc ctggcatgta tttatgggtg    3120
ctcgcgcttg atccattttg gtaagtgttg cttgggcatc agcgcgaata gcaccaatca    3180
cacacttta cctaatgacg ttttactgta ta                                   3212

<210> SEQ ID NO 5
<211> LENGTH: 2295
<212> TYPE: DNA
<213> ORGANISM: Artificial Sequence
<220> FEATURE:
<223> OTHER INFORMATION: parp2 coding region fro Zea mays
<220> FEATURE:
<221> NAME/KEY: misc_feature
<222> LOCATION: (107)..(2068)
<223> OTHER INFORMATION: open reading frame

<400> SEQUENCE: 5
tgacctgttc catcccgcca gcccttccgc tcccacgacc caaccccact gcccggagcc     60
cccgagccctt ctcgaatctt gcgagaaccc caggggcgag gagcagatgt cggcgaggct    120
acgggtggcg gacgtccgcg cggagcttca gcgccgcggc ctcgatgtat ccggcaccaa    180
gcctgctctc gtgcggaggc tggacgccgc aatttgcgag gcgagaagg ccgtggtggc     240
tgctgcgcca accagtgtgg caaatgggta tgacgtagcc gtagatggca aaaggaactg    300
cgggaataat aagaggaaaa ggtccgggga tgggggtgaa gagggaaacg gcgatacgtg    360
tacagatgtg acaaaactag agggcatgag ctatcgtgag ctgcagggat tggccaaggc    420
acgtggagtt gcggcaaatg ggggcaagaa agatgttatc cagaggttgc tctcggcgac    480
tgctggtcct gctgcagttg cagatggtgg tcctctgggc gccaaggaag tcataaaagg    540
tggtgatgag gaggttgagg tgaaaaagga gaagatggtt actgccacga gaagggagc    600
tgcagtgctg gatcagcaca ttcccgatca cataaaagtg aactatcatg tcttgcaagt    660
```

-continued

| | |
|---|---|
| gggcgatgaa atctatgatg ccaccttgaa ccagactaat gttggagaca acaacaataa | 720 |
| gttctatatc attcaagttt tagaatctga tgctggtgga agctttatgg tttacaatag | 780 |
| atggggaaga gttggggtac gaggtcaaga taaactacat ggtccctccc caacacgaga | 840 |
| ccaagcaata tatgaatttg aggggaagtt ccacaacaaa accaataatc attggtctga | 900 |
| tcgcaagaac ttcaaatgtt atgcaaagaa atacacttgg cttgaaatgg attatggtga | 960 |
| aactgagaaa gaaatagaga aaggttccat tactgatcag ataaaagaga caaaacttga | 1020 |
| aactagaatt gcgcagttca tatccctgat ctgcaatatt agcatgatga agcaaagaat | 1080 |
| ggtggaaata ggttataatg ctgaaaagct tccccttgga aagctaagga agctacaat | 1140 |
| acttaagggt tatcatgttt tgaaaaggat atccgatgtt atttcaaagg cggacaggag | 1200 |
| acatcttgag caattgactg gggaattcta caccgtgatt cctcatgact ttggtttcag | 1260 |
| aaagatgcgt gaatttatta tcgatactcc tcagaaacta aaagctaagc tggagatggt | 1320 |
| tgaagccctt ggtgagattg aaattgcaac taaacttttg gaggatgatt caagtgacca | 1380 |
| ggatgatccg ttgtatgctc gatacaagca acttcattgt gatttcacac tcttgaagc | 1440 |
| tgattcagat gagtactcta tgataaaatc atatttgaga atacacatg gaaaaacaca | 1500 |
| ctctggttat acggtggaca tagtgcaaat atttaaggtt tcaaggcatg gtgaaacaga | 1560 |
| gcgatttcaa aaatttgcta gtacaagaaa taggatgctt ttgtggcatg ttctcggtt | 1620 |
| gagcaactgg gctgggatcc tttctcaggg tctgcgaatc gctcctcctg aagcacctgt | 1680 |
| tactggttac atgtttggca agggtgttta ctttgctgac atgttttcaa agagtgcaaa | 1740 |
| ctattgctac gcctctgaag catgtagatc tggagtactg cttttatgtg aggttgcatt | 1800 |
| gggcgatatg aatgagctac tgaatgcaga ttacgatgct aataacctgc ccaaaggaaa | 1860 |
| attaagatcc aagggagttg gtcaaacagc acctaacatg gtcgagtcta aggtcgctga | 1920 |
| cgatggtgtt gttgttcccc ttggcgaacc caaacaggaa ccttccaaaa ggggtggctt | 1980 |
| gctttataat gagtacatag tgtacaacgt agaccagata agaatgcggt atgtcttaca | 2040 |
| tgttaacttc aatttcaaga acggtagat gttgcaaaga gctgaaactg ttgctgagat | 2100 |
| cttagcagaa catatgtgga cttatagcac caggtgccct cagcctcatt ttctgagcaa | 2160 |
| atttggtagc ctttgcattt cgattttggt ttcagcttct agccccattg atgattgata | 2220 |
| ctgagtgtat atatgaacca ttgatatcca ccttccatgt acttaagttt ttttaacatg | 2280 |
| tcccatgcat aataa | 2295 |

<210> SEQ ID NO 6
<211> LENGTH: 1384
<212> TYPE: DNA
<213> ORGANISM: Artificial Sequence
<220> FEATURE:
<223> OTHER INFORMATION: parp2 partial coding region from cotton
<220> FEATURE:
<221> NAME/KEY: misc_feature
<222> LOCATION: (3)..(460)
<223> OTHER INFORMATION: Open reading frame

<400> SEQUENCE: 6

| | |
|---|---|
| gagaagatbg ttacagcgac gaggaagggg tggctgttct ggatcaaggg atcccagatg | 60 |
| acataaaggc tcattatcat gttctacaaa agggtgatga tatctatgat gccatgttaa | 120 |
| atcagacgaa tgttgggcaa aacaataaca aattctttgt gatccagctt ctagaatctg | 180 |
| atgactcgaa gacatacatg gttcataaca gatggggtag agttggtgtg aagggtcaaa | 240 |
| ttaagttaca tggcccctt acttcacgac aagccgcaat tgatgagttt caaaccaaat | 300 |

-continued

| | |
|---|---|
| tctttaacaa gaccaaaaac tattggtaca acagaaaaga ctttgtttgt cacccaaagt | 360 |
| gctacacctt gctggagatg gactatgatg aaaaagaaaa ggaatctgat gtcaaagaa | 420 |
| aggctaactc ttccattggt gctcaattgc gggagacaaa gcttgaacaa cgtgttgcta | 480 |
| agtttatctc tattatatgc aatatcagca tgatgaagca acaaatgatg aaataggat | 540 |
| acaatgctga caagttgcct cttggtaagc taagcaaatc cacaatttta aagggtatg | 600 |
| atgtcttaaa gaaaattgct gatgtgattg accagtcaaa caggagcaag cttgagcaat | 660 |
| taagttcgga attttacacc gtgattccac atgattttgg atttagaaaa atgcgtgatt | 720 |
| ttgtcatcga cacacctcag aagttgaaaa agaagttgga aatggttgaa gccctgggag | 780 |
| aaatagaggt cgcatcaaaa ttattaatgg atgacattac gatggaggaa gatcctttat | 840 |
| attatcggta ccaacagctt cactgtgaac tgtttcctct tgacaatgat actgaggagt | 900 |
| tcgctttgat tgtaaagtat attcagaata ctcatgctca gacacattca aattatacag | 960 |
| ttgatgttgt tcaaatattc aaggtgacaa gagacggtga aagtgaacgc tttaaaaagt | 1020 |
| tttctggaac aaaaaataga atgctgttgt ggcatggttc tcggcttact aactggactg | 1080 |
| gcattctgtc ccaaggtttg cgcattgctc cacctgaagc gcctgccacg ggttatatgt | 1140 |
| ttgggaaggg ggtttacttt gctgatatgt tctccaaaag tgcaaattat tgctatacta | 1200 |
| attctgcctt cacaacaggg gtgttgcttc tatgtgaggt tgccctgggt gacatggctg | 1260 |
| agcttctaca agctaaaagc gatgctgata agctgccgga tgggaagttg agcacaaaag | 1320 |
| gtgttggtgc aactgcaccg gatccttctg aagcccagtc acttgatgat ggtgttgttg | 1380 |
| ttcc | 1384 |

<210> SEQ ID NO 7
<211> LENGTH: 1647
<212> TYPE: DNA
<213> ORGANISM: Arabidopsis thaliana

<400> SEQUENCE: 7

| | |
|---|---|
| atggagaatc gcgaagatct taactcaatt cttccgtacc ttccacttgt aattcgttcg | 60 |
| tcgtcgctgt attggccgcc gcgtgtggtg gaggcgttaa aggcaatgtc tgaaggacca | 120 |
| tctcacagcc aagttgactc aggagaggtt ctacggcaag ctattttcga tatgagacga | 180 |
| tccttatctt tctctactct cgagccatct gcttctaatg ctacgcatt tctctttgac | 240 |
| gaattgattg atgagaaaga atcaaagaga tggttcgatg agattatccc agcattggcg | 300 |
| agcttacttc tacagtttcc atctctgtta gaagtgcatt tccaaaatgc tgataatatt | 360 |
| gttagtggaa tcaaaaccgg tcttcgtttg ttaaattccc aacaagctgg cattgttttc | 420 |
| ctcagccagg agttgattgg agctcttctt gcatgctctt tcttttgttt gtttccggat | 480 |
| gataatagag gtgcaaaaca ccttccagtc atcaactttg atcatttgtt tgcaagcctt | 540 |
| tatataagtt atagtcaaag tcaagaaagc aagataagat gtattatgca ttactttgaa | 600 |
| aggttttgct cctgcgtgcc tattggtatt gtttcatttg aacgcaagat taccgctgct | 660 |
| cctgatgctg atttctggag caagtctgac gtttctcttt gtgcatttaa ggttcactct | 720 |
| tttgggttaa ttgaagatca acctgacaat gctctcgaag tggactttgc aaacaagtat | 780 |
| ctcggaggtg gttccctaag tagagggtgc gtgcaggaag atacgcttt catgattaac | 840 |
| cctgaattaa tcgctggcat gcttttcttg cctcggatgg atgacaatga agctatagaa | 900 |
| atagttggtg cggaaagatt ttcatgttac acagggtatg catcttcgtt tcggtttgct | 960 |
| ggtgagtaca ttgacaaaaa ggcaatggat cctttcaaaa ggcgaagaac cagaattgtt | 1020 |

-continued

```
gcaattgatg cattatgtac accgaagatg agacacttta agatatatg tcttttaagg    1080 gaaattaata aggcactatg tggctttta aattgtagca aggcttggga gcaccagaat    1140
atattcatgg atgaaggaga taatgaaatt cagcttgtcc gaaacggcag agattctggt    1200
cttctgcgta cagaaactac tgcgtcacac cgaactccac taaatgatgt tgagatgaat    1260
agagaaaagc ctgctaacaa tcttatcaga gattttatg tggaaggagt tgataacgag    1320
gatcatgaag atgatggtgt cgcgacaggg aattggggat gtggtgtttt tggaggagac    1380
ccagagctaa aggctacgat acaatggctt gctgcttccc agactcgaag accatttata    1440
tcatattaca cctttggagt agaggcactc cgaaacctag atcaggtgac gaagtggatt    1500
ctttcccata aatggactgt tggagatctg tggaacatga tgttagaata ttctgctcaa    1560
aggctctaca agcaaaccag tgttggcttc tttttcttggc tacttccatc tctagctacc    1620
accaacaaag ctatccagcc gccttga                                        1647

<210> SEQ ID NO 8
<211> LENGTH: 598
<212> TYPE: DNA
<213> ORGANISM: Solanum tuberosum

<400> SEQUENCE: 8
gcaatggaga atagaagaa cgtgaagtca atccttccct ttttgccggt gtgtctccga      60
tcatcttctc ttttctggcc gccgctagtt gttgaagcac tgaaagccct ctctgaaggc    120
cctcattaca gcaatgttaa ctccggccaa gtcctcttcc tcgcaatctc cgacattcgg    180
aattcccttt cactacctga ttcttcaatt tcctcttctg cttcagacgg attttctctc    240
ttatttgatg atttaattcc tagggatgaa gctgttaaat ggttcaaaga agtggtgccg    300
aaaatggcgg atttgctatt gcggttgcct tccttattgg aggctcacta tgagaaggct    360
gatggtggaa ttgttaaagg agtcaacact ggtcttcgct tattggaatc acaacagcct    420
ggcattgttt tcctcagtca ggaattagtc ggtgctcttc ttgcatgttc cttcttttgc    480
tattccctac caatgataga ggtatctgta tgatcagtat gacgagaaat ttgaaaataa    540
attgaagtgc attcttcact attttgagag gattggctca ttgatacctg cgggctac     598

<210> SEQ ID NO 9
<211> LENGTH: 1530
<212> TYPE: DNA
<213> ORGANISM: Oryza sativa

<400> SEQUENCE: 9
atggaggcgc gcggcgacct gcgctcgatc ctgccctacc tccccgtcgt gctccgcggc      60
ggcgcgctct ctggccgcc ggcggcgcag gaggcgctca aggcgctggc gctgggcccc    120
gacgtgagcc gcgtctcctc cggcgacgtc ctcgccgacg ccctcaccga cctccgcctc    180
gcgctcaacc tcgacccact cccgcgccgc gcgccgaggg gcttcgcgct cttcttcgac    240
gacctcctgt cgcgggcgca ggcgcgggac tggttcgacc acgtcgcccc ctcccctcgcc    300 cgcctcctcc tccgcctccc cacgctgctc gagggccact accgcgccgc cggcgacgag    360
gctcgcgggc tccgcatcct gagctcgcag gatgccgggc tcgtgctcct cagccaggag    420
ctcgccgccg cgctgctcgc ctgcgcgctc ttctgcctgt tccccaccgc cgatagggcc    480
gaggcgtgcc tcccggcgat caatttcgat agcctatttg cggcactgtg ttataattcg    540
aggcaaagcc aggagcagaa ggtgaggtgc cttgttcact attttgacag ggtgaccgct    600
tctacaccta ctggttccgt ttcgtttgag cgtaaggttc ttcctcgccg tcctgaatct    660
```

-continued

| | |
|---|---|
| gatggcatta cgtaccctga catggatact tggatgaaat ctggtgttcc cctttgcaca | 720 |
| ttccgggtat tttcctcagg cttgatagaa gatgaggaac aagaagccct gaagttgac | 780 |
| tttgcaaata gatatttggg aggtggcgca cttccagag gctgcgtgca ggaagaaatc | 840 |
| cggttcatga taaacccaga attgatcgtg ggcatgctct tcatggtttc aatgaagat | 900 |
| aatgaagcta tagaaattgt tggtgcagaa aggttctcac agtacatggg gtatggttcc | 960 |
| tcattccgtt ttactggtga ctacttagat agcaaaccct tgatgcgat gggtagacgg | 1020 |
| aaaactagga tagtggcaat tgatgctttg gactgtccaa ctaggttaca gtttgaatct | 1080 |
| agtggtcttc taagggaagt gaacaaggct ttttgtggat ttttggatca atcaaatcat | 1140 |
| cagctctgtg caaagcttgt ccaggattta aatacaaagg ataactgtcc aagtgtcatt | 1200 |
| cctgatgaat gcataggagt ttcaactgga aactggggtt gcgggctttt ggtggaaac | 1260 |
| cctgaaatca agagcatgat tcaatggatt gctgcatcac aggcactccg atcttttatt | 1320 |
| aactactaca cttttgagtc cgaatcactg aaaagattag aagaggtgac ccagtggata | 1380 |
| ttgcgccata ggtggacggt tggcgagttg tgggacatgc ttgtggagta ttcatcccag | 1440 |
| aggctaagag gagacaccaa tgagggcttt taacatggc tacttcccaa ggacatcccc | 1500 |
| aatggtgatg tagattacat gtgtgaatag | 1530 |

<210> SEQ ID NO 10
<211> LENGTH: 603
<212> TYPE: DNA
<213> ORGANISM: Zea mays

<400> SEQUENCE: 10

| | |
|---|---|
| tagggctgtg tgcaggagga aatccgcttc atgataaacc cgaattgat tgtgggtatg | 60 |
| ctattcttgt cttgtatgga agataacgag gctatagaaa tctttggtgc agaacggttc | 120 |
| tcacagtata tgggttatgg ttcctccttt cgctttgttg gtgactattt agataccaaa | 180 |
| cccctttgatt cgatgggcag acggagaact aggattgtgg ctatcgatgc tttggactgt | 240 |
| ccagctaggt tacactatga atctggctgt ctcctaaggg aagtgaacaa ggcattttgt | 300 |
| ggattttcg atcaatcgaa acaccatctc tatgcgaagc ttttccagga tttgcacaac | 360 |
| aaggatgact tttcaagcat caattccagt gagtacgtag gagtttcaac aggaaactgg | 420 |
| ggttgtggtg cttttggtgg aaaccctgaa atcaagagca tgattcagtg gattgctgca | 480 |
| tcacaggctc ttcgcccttt tgttaattac tacacttttg agaacgtgtc tctgcaaaga | 540 |
| ttagaggagg tgatccagtg gatacggctt catggctgga ctgtcggcga gctgtggaac | 600 |
| ata | 603 |

<210> SEQ ID NO 11
<211> LENGTH: 651
<212> TYPE: DNA
<213> ORGANISM: Saccharomyces cerevisiae

<400> SEQUENCE: 11

| | |
|---|---|
| atgaagactt taattgttgt tgatatgcaa aatgatttta tttcaccttt aggttccttg | 60 |
| actgttccaa aaggtgagga attaatcaat cctatctcgg atttgatgca agatgctgat | 120 |
| agagactggc acaggattgt ggtcaccaga gattggcacc cttccagaca tatttcgttc | 180 |
| gcaaagaacc ataaagataa agaaccctat tcaacataca cctaccactc tccaaggcca | 240 |
| ggcgatgatt ccacgcaaga gggtattttt tggcccgtac actgtgtgaa aaacaccctgg | 300 |
| ggtagtcaat tggttgacca aataatggac caagtggtca ctaagcatat taagattgtc | 360 |

```
gacaagggtt tcttgactga ccgtgaatac tactccgcct tccacgacat ctggaacttc    420
cataagaccg acatgaacaa gtacttagaa aagcatcata cagacgaggt ttacattgtc    480
ggtgtagctt tggagtattg tgtcaaagcc accgccattt ccgctgcaga actaggttat    540
aagaccactg tcctgctgga ttacacaaga cccatcagcg atgatcccga agtcatcaat    600
aaggttaagg aagagttgaa ggcccacaac atcaatgtcg tggataaata a            651
```

<210> SEQ ID NO 12
<211> LENGTH: 1290
<212> TYPE: DNA
<213> ORGANISM: Saccharomyces cerevisiae

<400> SEQUENCE: 12

```
ttaggtccat ctgtgcgctt cgttatcacc actccaactt cgttcagtat atcccaattc     60
ctctttcact ctcttcacag tggcaggatc tcccatattt ttacctaagt tatcagaaat    120
tttgatagcg tgattaccat ttacttctaa tagtttgata acgatgttta acggctcact    180
tttaacctgg ggttctgact tcttacgaaa atcattagta aagtttgtgc caataccgaa    240
tgtggctagc attccattct ctttagctgc atggggagtaa gttattgcct tttcgacgtt    300
caaagaatcg gaataacaga taatcttcga gaatttaggc aatttcaaca cgtcatggta    360
atggtgggaa atcttttttgg tatactcaac tgggtctcca gaatcttgtc taacaccgac    420
gtaagcatca gaatatggtg gacggaatga ttttaaaaag tcatcagttc caaaagtatc    480
cgttaatgct aaaccagcat ttttttgcacc aaaagtattg atccaacaat ccattgcatt    540
tttattggca tgcaaataat cttcactaat agaagcgact cccataaccc actcgtgagc    600
cacagtaccg attggcttga ctccatattt cttggcaaat aaaatatttg atgtgcctaa    660
taatagcgat ttgtttctgt ctgggttacc gttcacagct ttcatgattc cttgcataat    720
tagatcttga gccttcagag atctacgacg tcttgtacca aattcactga atctaatacc    780
attatcaaac aaagtttccg ccttcttctc agcttgttct aattggtttt cgtagtccca    840
gtcgatgtca acaaatttaa atacgcttc tgatattagg gacagtaagg ggatctcata    900
aaggatagta tccttccaac taccactgac taaaattttc aatttgtagt gggtgggctt    960
gccctcgatt tcttctgaag tgaaggaaat ctgctcttca gggtgtagtt tgtaattaga   1020
actgctaata tacttaatat atgccgatgg caaatatggg atttcctgtt ttaagtattc   1080
aatttcctct tctgtgaacc tcaaatttcc caaatacgaa aattgctctt tcaaccaatt   1140
aatggcttcc ttattgaagg tcaattggga cgacctgttg gtatatttat aagtaactgt   1200
aacatctgga aaattagtga agacagcagc atgcatcgta atcttgtaca tgtctgtgtc   1260
caaaagagac tttatcactg gttctgacat                                     1290
```

<210> SEQ ID NO 13
<211> LENGTH: 1206
<212> TYPE: DNA
<213> ORGANISM: Saccharomyces cerevisiae

<400> SEQUENCE: 13

```
atggatccca caagagctcc ggatttcaaa ccgccatctg cagacgagga attgattcct     60
ccacccgacc cggaatctaa aattcccaaa tctattccaa ttattccata cgtcttagcc    120
gatgcgaatt cctctatagta tgcacctttt aatattaaga ggaagaaaaa gcatcctaag    180
catcatcatc accatcatca cagtcgtaaa gaaggcaatg ataaaaaaca tcagcatatt    240
ccattgaacc aagacgactt tcaaccactt tccgcagaag tgtcttccga agatgatgac    300
```

-continued

```
gcggatttta gatccaagga gagatacggt tcagattcaa ccacagaatc agaaactaga      360
ggtgttcaga aatatcagat tgctgattta gaagaagttc cacatggaat cgttcgtcaa      420
gcaagaacct tggaagacta cgaattcccc tcacacagat tatcgaaaaa attactggat      480
ccaaataaac tgccgttagt aatagtagca tgtgggtctt tttcaccaat cacctacttg      540
catctaagaa tgtttgaaat ggctttagat gcaatctctg aacaaacaag gtttgaagtc      600
ataggtggat attactcccc tgttagtgat aactatcaaa agcaaggctt ggccccatcc      660
taccatagag tacgtatgtg tgaattggcc tgcgaaagaa cctcatcttg gttgatggtg      720
gatgcatggg agtcattgca accttcatac acaagaactg ccaaggtctt ggatcatttc      780
aatcacgaaa tcaatattaa gagaggtggt gtagctactg ttactggaga aaaaattggt      840
gtgaaaataa tgttgctggc tggtggtgac taatagagt caatgggtga accaaacgtt       900
tgggcggacg ccgatttaca tcacattctc ggtaattacg gttgtttgat tgtcgaacgt      960
actggttctg atgtaaggtc ttttttgtta tcccatgata ttatgtatga acatagaagg     1020
aatattctta tcatcaagca actcatctat aatgatattt cttccacgaa agttcgtcta     1080
tttatcagac gcgccatgtc tgtacaatat ttgttaccta attcggtcat caggtatatc     1140
caagaacata gactatatgt ggaccaaacc gaacctgtta agcaagttct tggaaacaaa     1200
gaatga                                                                1206
```

<210> SEQ ID NO 14
<211> LENGTH: 1188
<212> TYPE: DNA
<213> ORGANISM: Saccharomyces cerevisiae

<400> SEQUENCE: 14

```
atggatccca ccaaagcacc cgattttaaa ccgccacagc caaatgaaga actacaacca       60
ccgccagatc caacacatac gataccaaaa tctggaccca tagttccata tgttttagct      120
gattataatt cttcgatcga tgctcctttc aatctcgaca tttacaaaac cctgtcgtca      180
aggaaaaaaa acgccaactc aagcaaccga atggaccata ttccattaaa tactagtgac      240
ttccagccac tatctcggga tgtatcatcg gaggaggaaa gtgaagggca atcgaatgga      300
attgacgcta ctctacagga tgttacgatg actgggaatt tggggggtact gaagagccaa      360 attgctgatt tggaagaagt tcctcacaca attgtaagac aagccagaac tattgaagat      420
tacgaatttc ctgtacacag attgacgaaa aagttacaag atcctgaaaa actgcctctg      480
atcatcgttg cttgtggatc atttctcccc ataacatacc tacatttgag aatgtttgaa      540
atggctttag atgatatcaa tgagcaaacg cgttttgaag tggttggtgg ttatttttct      600
ccagtaagtg ataactatca aaagcgaggg ttagccccag cttatcatcg tgtccgcatg      660
tgcgaattag catgcgagcg gacatcatct tggttaatgg ttgatgcctg ggaatcttta      720
caatcaagtt atacaaggac agcaaaagtc ttggaccatt tcaatcatga aataaatatc      780
aagagaggtg gaatcatgac tgtagatggt gaaaaaatgg gcgtaaaaat catgttattg      840
gcaggcggta tcttatcga atccatgggc gagcctcatg tgtgggctga ttcagacctg      900
caccatattt tgggtaatta tggatgtttg atcgtggaaa ggactggttc tgatgttagg      960
tccttcttgc tttcccatga tatcatgtat gaacacagaa gaaatatcct tattatcaaa     1020
caacttattt acaatgatat ttcctctacg aaagtgcggc ttttcatcag acgtggaatg     1080
tcagttcaat atcttcttcc aaactctgtc atccgttaca tccaagagta taatctatac     1140
attaatcaaa gtgaaccggt caagcaggtc ttggatagca aagagtga                   1188
```

<210> SEQ ID NO 15
<211> LENGTH: 2145
<212> TYPE: DNA
<213> ORGANISM: Saccharomyces cerevisiae

<400> SEQUENCE: 15

```
atgtcacatc ttatcacttt agctacatgc aacttgaatc aatgggccct agattttgaa        60
ggtaatagag accgtatcct acagtccatt aagattgcca agagaggggg tgccaggtta       120
cgtgtcggcc cagaactgga ataactggc tacggatgtt tagatcattt tttagaaaat        180
gacgtttgcc ttcattcatg ggaaatgtat gctcaaatca ttaagaataa agaaacccat       240
ggattaatac ttgacattgg tatgcccgtt ctacacaaga atgttcgtta taattgtcgt       300
ttgttatcct tggatggtga gatattgttc ataagaccta agatttggtt agctaatgat       360
ggtaactata gggaaatgag atttttcaca ccttggatga aacctggcgt ggtggaggac       420
tttatccttc cacctgagat tcagaaagtt accggccaga gacttgtgcc atttggggac       480
gctgtgataa attcattgga tacatgcatt ggtacagaaa cttgtgaaga attgtttaca       540
cctcaatccc cccacatcgc catgtcttta gatggtgtgg aaatcatgac aaactcatct       600
ggttctcatc atgaactgcg taagttaaat aaaaggttag acctaatttt aaatgccact       660
aaacgttgtg gtggtgttta cttgtatgca aatcaaagag ttgtgatgg tgacagatta       720
tattatgatg gctgtgcact aattgccatc aatggtacaa ttgtagccca aggttcacaa       780
ttttcgctag atgatgtgga gtagttact gctactgtgg acctagaaga ggtgaggagt       840
tatcgtgcag ctgtcatgtc tcgtggccta caagcctcct tggcagaaat aaagttcaag       900
cgtattgata tcctgtagaa attggcttta atgacctcca gatttgatcc tacagtgtgt       960
ccaacaaaag tccgcgagcc tttctatcac tctcctgagg aagaaattgc actgggacct      1020
gcttgctgga tgtgggatta tttaagacgt tgtaacggaa cagggttttt ccttcccta      1080
tctgggggca ttgactcttg tgcaactgca atgattgtcc actctatgtg ccgtttagtg      1140
accgacgctg ctcaaaatgg aaatgagcaa gttatcaaag acgttcgtaa gataacacgt      1200
agcggcgatg attggattcc agacagtcca caggatctag cctcaaaaat atttcactcc      1260
tgtttcatgg gtacggaaaa ttcatccaag gagacaagaa acagagcaaa ggaccttcc       1320
aatgcaattg gatcttacca cgtggattta agatgggact cattggtatc cagtgtggtg      1380
tccttattcg aagtagccac tggcaaaaaa ccaatataca aatatttgg gggatctcaa       1440
atcgagaact ggctttaca aaacatccag gcgcgtctaa gaatggttct ttcttatctt       1500
tttgcgcaac tgttgccgtg ggttcgtggt atcccaaact cgggtggatt gttagtactt      1560
ggtagcgcaa atgttgatga gtgcttacgt gggtatctaa caaatatga ctgctcctcc       1620
gcagatatca accctattgg gggtatttca aaaactgact tgaaaagatt cattgcctac      1680
gcatcaaaac aatataacat gccaatcttg aatgactttt taaacgctac accaactgca      1740
gaattagaac ctatgactaa agattacgtt caatcggatg agatagatat ggggatgacg      1800
tatgaagaat tgggcgtgtt tggttaccta agaaaggttg aaaatgtgg tcttattct       1860
atgttcttaa aacttcttca tcaatggtcc ccaaagttaa cacctcgtca atatctgaa       1920
aaggtgaaaa gattttctt cttctatgcc atcaacagac acaagcaaac tgttttaact      1980
cctagttatc atgctgaaca gtattcacca gaagacaaca gatttgactt acgtcctttc      2040
ttaatcaacc caagatttcc atgggcttca agaaaaattg atgaagttgt cgagcagtgt      2100
gaagcacata aaggctcaac gcttgacatt atgtctattg attag                      2145
```

```
<210> SEQ ID NO 16
<211> LENGTH: 597
<212> TYPE: DNA
<213> ORGANISM: Arabidopsis thaliana

<400> SEQUENCE: 16
atggcttcct catcaacgag aaagtacgag acacgaaagc gagatccaaa ctctaaaatc      60
gcagctcttc tcgttatcga catgcagaat cacttctcct ccatggccaa acccatcctc     120
aacaacgttc tcaccaccat cgacatctgc cgacgcgcct cagtccccgt attctttacg     180
cgtcacaacc acaaatcccc gaccgaccac ggcatgctcg gcgagtggtg taacggcgat     240
gtaatccttg acggaaccac cgattctgaa atcatccagg agatacaagg ccaagtaacc     300
ggaccagacg agatggtgga agaacacg tacagtgcgt ttaacaaaac ccgcctccag      360
gaaaacctgg aaagatcgg agtaaaggag gtgatcgtga tcggagtgat gacgaacttg     420
tgctgtgaga caacgcgcg tgaagcgttt attaagggtt ttagggtttt tttctcgacg     480
gacgcgactg cgacgtttaa tgaggagctt cacgaggcta cgctaatgaa tctcgctttt     540
ggcttcgctt atctcgtcga ttgcgataaa ctccggcgaa gtctactcgg taactaa       597

<210> SEQ ID NO 17
<211> LENGTH: 597
<212> TYPE: DNA
<213> ORGANISM: Arabidopsis thaliana

<400> SEQUENCE: 17
atggcttctt catcatcgag aacgtacgag acacgaaagc gagagccaaa tcctaaaatc      60
gcagctcttc tcgtcatcga tatgcagaat cacttctact ctatggctga accaatcctc     120
caaaacgctc tcaccaccat cgacatctgc cgacgcgctt caatccccgt attcttcacg     180
cgccacaacc acaaatcccc aaccgaccac ggcatgctcg gagagtggtg gaacggcgat     240
ctaatcctcg acggaaccac tgattccgaa atcatcccgg aaatcaatcg ccaggtcacc     300
ggaccagacg aaatcgtgga agagcacacg tacagtgcgt ttaacaacac gcaccttcag     360
gagaagctgg acaagatcgg agtgaaggag gtgatcgtta tcggagtgat gacgaaccta     420
tgctgtgaga cgacggcgcg tgaagcgttt gtaaggggt ttagggtttt tttctcgacg      480
gacgcgactg cgacggttaa tgaggagctt cacgaggcta ctctaatgaa tctcgcgtat     540
ggctttgctt atctcgtcga ttgcgataga ctccggcgag gtctactcag tagttaa       597

<210> SEQ ID NO 18
<211> LENGTH: 591
<212> TYPE: DNA
<213> ORGANISM: Arabidopsis thaliana

<400> SEQUENCE: 18
atggccgaga gatggaggaa cacggctcta ctcgtcatcg acatgcagaa cgatttcata      60
gaggaaggtg ctgtgacgca agtgaaagga ggaaaatcta tagttcctaa tgttatcaga     120
gtcgtcgaac tcgcgaggca gcgtggtatt tcgtaatttt ggttgttcg agaacatgat      180
cgtcaaggaa gagatgttga attattcagg cgccataact acagttctga aaagtcggg      240
ccagttatta aaggcaccgt aggagcagaa ttggttgatg gattgatgat caacgaagaa     300
gatgactata agattgtgaa aactcgtttc agtgctttct ttagtaccaa tcttcattcc     360
ttcttgcaaa cttcaggggt taccaagtta gtgattgctg gtgtgcaaac gccgaactgt     420
atccggcaaa cggtgtttga tgcagtggcg ctggattatc ccaatgtgac tgttattaca     480
```

```
gatgccacag ctgctgcaac accagagatc catactgcga atattcttga catgaagaat      540
attggagtca agactcctac attacacgag tggtccgaag aacttgcttg a              591
```

<210> SEQ ID NO 19
<211> LENGTH: 1680
<212> TYPE: DNA
<213> ORGANISM: Arabidopsis thaliana

<400> SEQUENCE: 19

```
atggagaaga agaaaatggt ctcgatgga agcaatcgg gtcgggtcat aacggaccc       60 actaacccga tggtcacacc tctgctcaac gatctttacc aattcaccat ggcttatgct   120
tattggaaag ctggcaaaca atctgagcga tctgtgtttg atctgtattt tcgtaagaat   180 cctttggtg gagaatacac tatctttgct ggtttagaag aatgcatcaa atttctcgct   240
aatttcaatt tgactgatga agagatcgat ttcgttcgtg attcgttacc tggatgtgag   300
gaagcttcct gtgattatct tcagggctt gattgttctg acattgaagt gtatgccatt   360
tcggaaggat cagttgtttt tcctaaagtt cctttactca gaatcgaagg tcctgttgct   420
gtggtgcaat tgttggaaac tccattcctc aatctcatca attacgcatc tttggttgct   480
acaaatgcag caagacatcg gtttgttgca ggaaaatcta agcttctgct tgagtttggt   540
gctagaagag ctcagggacc cgatggtgca ataagcgcat caagtattg ctaccttgga    600 ggttttgatg caacaagtaa tgttgcagcg ggaaaactgt ttgggatacc cctccgtggt   660
actcattccc atgctttgt tagctcattc atgagccttg atgaaattgt tgacaaagtg   720
cttcgaagtt ctgatgggaa aagcacttgt aaggatttta tatgtttggt ccaaacttgc   780
ctaacaaaga ttcagaattc atcttcatta caaggaattt tttccgagac aaatcaaagc   840
gagcttgcag cgttcatttc atatgcactg gcattcccaa actcctttct cgctcttgta   900
gacacttatg atgtgatgaa gagtggtatt ccaaacttct gtgctgttgc tctagcactt   960
aatgaattgg gatacaaagc agtaggcatt agactggatt caggtgactt agcctatctt  1020
tctactgagg tcaggaaatt ctttgtgcc atagagaag acctcaaagt tcctgatttc    1080
gggaagatga tcgtcactgc tagtaacgat ctaaacgaag agacagtcga tgctctaaat  1140
aaacagggtc atgaagtaga tgcatttgga attggaacca acttagtgac ttgctatgcg  1200
caagctgcgt taggttgtgt tttcaaactt gtggaaataa acaatcagcc tcggatcaaa  1260 cttttctgaag atgttactaa ggtatcgatt ccatgtaaaa agcgtactta cagattgttc  1320
ggaaaagagg gttaccctct tgttgatata atgactggag agaacgaacc acctccaaag  1380
gtcggtgaaa ggttacttg ccgtcatcca ttcaatgaat caaaaagggc ttatgtggtt    1440
ccacaacgcg ttgaagagct tctgaaatgt tattggcgtg gcaatgcaga tgaagctagg  1500
gaagagctag agccattgaa agagctaaga atcgttgca tcaaacagct cgaaaatatg    1560
cgacccgatc atatgagaag attaaaccct actccttata aggttagtgt cagcgccaag  1620
ttgtatgact tcatccactt cctctggctc aacgaagctc ctgtcggtga actgcattga  1680
```

<210> SEQ ID NO 20
<211> LENGTH: 1674
<212> TYPE: DNA
<213> ORGANISM: Arabidopsis thaliana

<400> SEQUENCE: 20

```
atggagccga agagaacgg ctcagaattg ggtcagaaga tcattgacgg accaacgaat      60
ccaatggtca cacctttact caatgatctt tatcaattca ccatggctta tgcttattgg   120
```

| | |
|---|---|
| aaagctggca aacacaacga acgatccgtt ttcgatctgt attttcgtaa gaacccattt | 180 |
| ggtggtgagt acactgtgtt tgctggatta aagagtgtg ttaagttctt agccaatttc | 240 |
| aaattgactg atgaagaaat cgatttcgtt caagagtgtt tgcctggatc tgaggaagct | 300 |
| ttttgtgatt atcttagagg gcttgattgt tctgatgttg aagtttatgc aattccggaa | 360 |
| ggatcagttg ttttttcctaa agtacctctc atgagagttg aaggacctgt tggtgttgtt | 420 |
| caattgttgg aaactccatt cctcaatctt gtcaattttg catctttggt agctactaac | 480 |
| gcagctaggc atcgctttgt tgccggaaaa tctaagagtc tactcgagtt tggtgctcga | 540 |
| agggctcagg gtccggatgg tgcaataagc gcatcaaaat attgctacct tggaggtttt | 600 |
| gatgcaacaa gtaatgtagc agctggaaaa cttttttggga ttcctcttcg tggaacacac | 660 |
| tctcatgctt atgttagctc attcatgagt actgatgaga ttgttgacaa agtacttcgt | 720 |
| agtgctgatg ggaaaaccac gtgcgaggat tttgttagtc atgttcagac atggttaaaa | 780 |
| aagattcagt attcaccatc tctaagtggc attttctctg agacaaatca aagcgagcta | 840 |
| gcagctttca cctcatatgc actggcattc cccaaaactt ttcttgccct cgtagataca | 900 |
| tacgatgtga tgaagagtgg aatccctaac ttctgtgcag ttgctttagc actcaatgac | 960 |
| tttggatata aagcattagg tattagactg gattcaggtg atttagctta tctatctaga | 1020 |
| gaggccagaa atttcttctg cacggtagag agagaactaa aagtgcctgg ttttgggaag | 1080 |
| atggtcgtca ctgctagtaa tgatctaaat gaagagacga ttgacgcttt aaataaacag | 1140 |
| ggacatgagg tggatgcttt tggcatcggg acctacttgg tcacttgcta ttcacaagcg | 1200 |
| gccttaggtt gcgttttcaa acttgtggag ataaacaatc agcctcggat taaactttct | 1260 |
| gaagatgtta caaggtatc aataccgtgt aaaaagcgaa gttacagatt atacggcaaa | 1320 |
| gaaggttacc ctctggtaga tataatgact ggagagaacg aaccacctcc aaaggttggt | 1380 |
| gagcgtttac tttgtcgtca cccattcaac gaatccaaaa gagcatatgt agtgccacaa | 1440 |
| cgtgtcgaag agctcctcaa atgttattgg cgtggaagtg cagatgaagc aagagaagta | 1500 |
| ttaccgccctt tgaaagagat aagagaccgt tgcatcaaac agctcgaaaa catgcgacct | 1560 |
| gatcatatga ggagattaaa cccaactcct tataaggtta gtgtaagcgc aaagctgtac | 1620 |
| gatttcatcc acttcttatg gctaaacgaa gcacctgttg gtgaattgca gtga | 1674 |

<210> SEQ ID NO 21
<211> LENGTH: 717
<212> TYPE: DNA
<213> ORGANISM: Arabidopsis thaliana

<400> SEQUENCE: 21

| | |
|---|---|
| atggatgtcc cgttaccagt cgagaaatta tcttatggat caaacactga ggacaaaact | 60 |
| tgtgtagtgc ttgtggcaac tgggagtttc aatcctccta ctttcatgca tttacgcatg | 120 |
| tttgagctgg cgagagatga attacgctca aaggatttc atgttcttgg aggatatatg | 180 |
| tctcctgtta atgatgcata taagaagaag ggccttttat ctgcagaaca tcgtttagag | 240 |
| atgtgtaatg tatcatgtca aagctctgac tttgtaatgg ttgatccgtg ggaggcatct | 300 |
| caaagcaact accaacgaac tttgacggtt ttatcaaggg tcaagacttt cttaacaaca | 360 |
| aatcgacatg tacccgagga atctctcaaa gtcatgctac tatgtggctc ggatttactg | 420 |
| ctatctttct gcactccggg tgtttggatc cctgaacagt taagaactat ttgcaaagat | 480 |
| tatggcattg tgtgcatccg tagagaagga caagatgttg aaaatatgat ctctggtgac | 540 |
| gaaatcttaa acgaaaactg tgctaacgtc aaaatcgttg acaatactgt tcctaatcaa | 600 |

| | |
|---|---:|
| atcagttcga gtagattaag gcaatgcatt tcgcgagggt tatcggttaa atacttgact | 660 |
| gaagatggag taatagatta tatcagacaa catcaactat acactgagct cacatga | 717 |

<210> SEQ ID NO 22
<211> LENGTH: 2178
<212> TYPE: DNA
<213> ORGANISM: Arabidopsis thaliana

<400> SEQUENCE: 22

| | |
|---|---:|
| atgaggctgt tgaaggttgc tacgtgtaac ttgaaccaat gggccatgga tttcgagagc | 60 |
| aacatgaaga acatcaaggc ttcgatcgct gaggcaaagg ctgctggtgc tgttatcagg | 120 |
| cttggacccg agctcgaggt cactggctat ggttgcgagg atcacttctt ggaactcgac | 180 |
| actgtcactc atgcgtggga gtgtttgaag gaattgctgc ttggtgattg acggatgat | 240 |
| attttgtgca gcataggaat gcctgtgatt aaggagcag agcgttataa ctgccaggtt | 300 |
| ctctgtatga acagaagaat catcatgatt cgaccgaaaa tgtggctcgc aaacgatgga | 360 |
| aactataggg agctacggtg gttcacagct tggaagcaga gagaagagct agaggaattt | 420 |
| cagctcccca ttgaaatttc agaggctttg gagcagaaat cagtcccttt tggttatggt | 480 |
| tacatccagt ttatcgacac ggctgttgca gctgaagtct gtgaggaact gtttagtcca | 540 |
| cttcctcctc atgccgagct cgcattgaat ggtgttgaag tatttatgaa tgcaagtggg | 600 |
| agtcatcacc aacttaggaa actagatatt cgtctgaatg cttttatggg ggctactcat | 660 |
| gctcgtggtg gggtgtatat gtacagtaat caacaaggat gcgatggtag ccgcttatac | 720 |
| tacgatggat gtgcatgtat tgttgtaaac gggaatgttg ttgctcaagg ctcacaattc | 780 |
| tcgttgagag acgttgaggt catcatttca caagtggatc ttgatgcggt tgctagcctt | 840 |
| cgtggatcta taagtagctt tcaggaacaa gcaagctgca aggttaaagt atcttcagta | 900 |
| gctgtgccct gtagacttac acagtccttc aacctgaaaa tgacactaag cagtccgaag | 960 |
| aagatcattt accactctcc acaagaagaa atagcctttg gtcccgcttg ctggatgtgg | 1020 |
| gactatttga gaagaagtgg cgcttcagga ttttttgcttc ctctttctgg cggagcagac | 1080 |
| agctcctccg tggcagctat tgttggctgc atgtgccaac ttgttgttaa agagattgca | 1140 |
| aagggagatg agcaagtaaa agctgatgcg aaccgaattg gaattatgc taatgggcag | 1200 |
| tttcctactg atagcaaaga gtttgccaaa cgaatatttt acactgtctt tatgggttct | 1260 |
| gaaaacagtt ctgaggagac aaaaaggcgt tcaaagcagc tggcagacga gattggtgct | 1320 |
| tggcatcttg atgtttgcat agatggtgtt gtctctgcag ttttatcatt atttcaaaca | 1380 |
| gttacaggca agcgaccaag gtataaggtt gatggaggat caaatgctga aaccttggg | 1440 |
| ttgcagaaca ttcaagcccg gatgagaatg gtgttagcat ttatgttagc gtctctcttg | 1500 |
| ccttgggttc atagcaaacc aggcttttac cttgttctag gcagctccaa cgttgatgaa | 1560 |
| ggacttcgtg gttacctgac aaagtatgat tgcagctcag cagacataaa tcctatagga | 1620 |
| agtatcagta aaatggattt gaggttgttc ttaaaatggg ctgcaacgaa tctcggatat | 1680 |
| ccatccttgg cagagataga agctgctcca ccaacagctg agcttgagcc cattcgttct | 1740 |
| gactattctc agctcgatga agtcgacatg gaatgacat atgaagagct ttcagtctat | 1800 |
| ggaaggatga ggaagatatt ccgttgtgga ccagtatcta tgttcaagaa tctatgttac | 1860 |
| aagtggggaa caaagctaag cccagcagaa gtagctgaga aagtgaagta tttcttcaaa | 1920 |
| tattattcga tcaatcgaca caaaatgact gtcctcacac cgtcttatca cgctgagagt | 1980 |
| tactccccag aggacaacag attcgatctg aggcagtttc tgtacaacag caagtggcca | 2040 |

-continued

```
taccagttta  agaagattga  cgagattgtt  gacagcttaa  atggtgactc  agttgctttc   2100
ccggaagaag  aagcaaactc  caacaaagaa  attggagttg  tagcagcaaa  ctccggagac   2160
ccaagtgcgg  gtctctga                                                     2178
```